US009707278B2

(12) United States Patent
Khleif et al.

(10) Patent No.: US 9,707,278 B2
(45) Date of Patent: Jul. 18, 2017

(54) METHODS OF MODULATING IMMUNE RESPONSES BY MODIFYING AKT3 BIOACTIVITY

(71) Applicant: Augusta University Research Institute, Inc., Augusta, GA (US)

(72) Inventors: Samir N. Khleif, Silver Spring, MD (US); Mikayel Mkrtichyan, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 14/689,517

(22) Filed: Apr. 17, 2015

(65) Prior Publication Data
US 2015/0343028 A1  Dec. 3, 2015

Related U.S. Application Data
(60) Provisional application No. 61/980,795, filed on Apr. 17, 2014.

(51) Int. Cl.
*A61K 48/00* (2006.01)
*A61K 38/00* (2006.01)
*A61P 31/04* (2006.01)
*A61K 38/45* (2006.01)

(52) U.S. Cl.
CPC ...... *A61K 38/45* (2013.01); *C12Y 207/11001* (2013.01)

(58) Field of Classification Search
USPC ...................................................... 514/44, 2
See application file for complete search history.

(56) References Cited

U.S. PATENT DOCUMENTS 6,809,194 B1 * 10/2004 Reinhard ............... C07H 21/04
435/325

OTHER PUBLICATIONS

Abu-Eid et al. (Cancer Immunol Res., 2014 vol. 2(11) 1080-1090).*
Printout from Uniprot describing gene Akt3 and the name of the protein encoded by the gene. Downloaded from http://www.uniprot.org/uniprot/Q9Y243 on Apr. 13, 2017.*
Carson, et al., "Impaired T cell receptor signaling in Foxp3+ CD4 T cells", Ann N Y Acad Sci.,, 1103:167-78 (2007).

(Continued)

*Primary Examiner* — Terra C Gibbs
(74) *Attorney, Agent, or Firm* — Smith Gambrell & Russell LLP

(57) ABSTRACT

Methods of decreasing an immune suppressive response, increasing an immune stimulating response, or a combination thereof in a subject in need thereof are disclosed. The methods typically include administering the subject a composition including a compound that reduces the bioavailability of Akt3 in an amount effective to reduce the immune suppressive response, increase the immune stimulating response, or a combination thereof in the subject.
Methods of increasing an immune suppressive response, decreasing an immune stimulating response, or a combination thereof in a subject in need thereof are also disclosed. The methods typically include administering the subject a composition including a compound that increases the bioavailability of Akt3 in an amount effective to increase the immune suppressive response, decrease the immune stimulating response, or a combination thereof in the subject.
Pharmaceutical compositions, combination therapies and vaccine formulations including modulators of Akt3 bioactivity are also provided.

6 Claims, 15 Drawing Sheets

(56) References Cited

OTHER PUBLICATIONS

Chen, et al., "Conversion of peripheral CD4+CD25− naive T cells to CD4+CD25+ regulatory T cells by TGF-beta induction of transcription factor Foxp3", J Exp Med., 198(12):1875-86 (2003).

Conery, et al., "Akt interacts directly with Smad3 to regulate the sensitivity to TGF-beta induced apoptosis", Nat Cell Biol., 6(4):366-72 (2004).

Crellin, et al., "Altered activation of AKT is required for the suppressive function of human CD4+CD25+ T regulatory cells", Blood, 109:2014-22 (2007a).

Crellin, et al., "Flow cytometry-based methods for studying signaling in human CD4+CD25+FOXP3+ T regulatory cells", J Immunol Methods, 324:92-104 (2007b).

Haxhinasto, et al., "The AKT-mTOR axis regulates de novo differentiation of CD4+Foxp3+ cells", J. Exp. Med., 205:565-74 (2008).

Li, et al., "CD4+CD25+ regulatory T-cell lines from human cord blood have functional and molecular properties of T-cell anergy", Blood, 106:3068-73 (2005).

Patton, et al., "The PI3K p110delta controls T-cell development, differentiation and regulation", Biochem. Soc. Trans., 35:167-71 (2007).

Patton, et al., "Cutting edge: the phosphoinositide 3-kinase p110 delta is critical for the function of CD4+CD25+Foxp3+ regulatory T cells", J. Immunology 177:6598-602 (2006).

Sauer, et al., "T cell receptor signaling controls Foxp3 expression via PI3K, Akt, and mTOR", PNAS, 105:7797-802 (2008).

Sharma, et al., "Targeting Akt3 signaling in malignant melanoma using isoselenocyanates", Clin Cancer Res., 15(5):1674-85 (2009).

Tsiperson, et al., "Suppression of inflammatory responses during myelin oligodendrocyte glycoprotein-induced experimental autoimmune encephalomyelitis is regulated by AKT3 signaling", J Immunol., 190(4):1528-39 (2013).

Walsh, et al., "PTEN inhibits IL-2 receptor-mediated expansion of CD4+ CD25+ Tregs", J. Clin. Invest., 116:2521-31. (2006).

Wang, et al., "Glycogen synthase kinase 3: a point of convergence for the host inflammatory response", Cytokine, 53(2):130-40 (2011).

Wen, et al., "The role of the transcription factor CREB in immune function", J Immunol., 185(11):6413-9 (2010).

Xaio, et al., "Transcriptional and translational regulation of TGF-beta production in response to apoptotic cells", J Immunol., 181(5):3575-85 (2008).

* cited by examiner

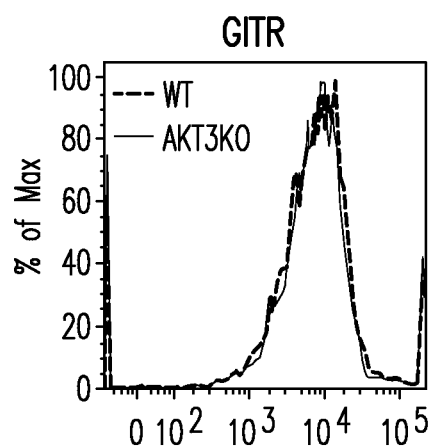
FIG.3A
FIG.3B
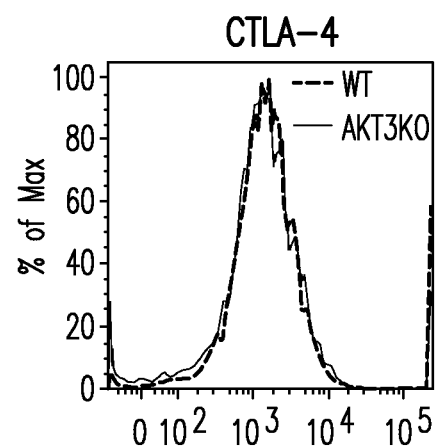
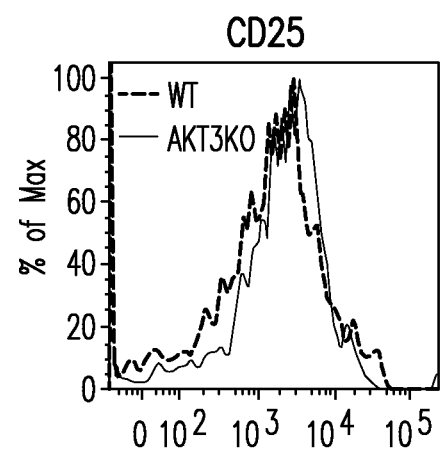
FIG.3C
FIG.3D

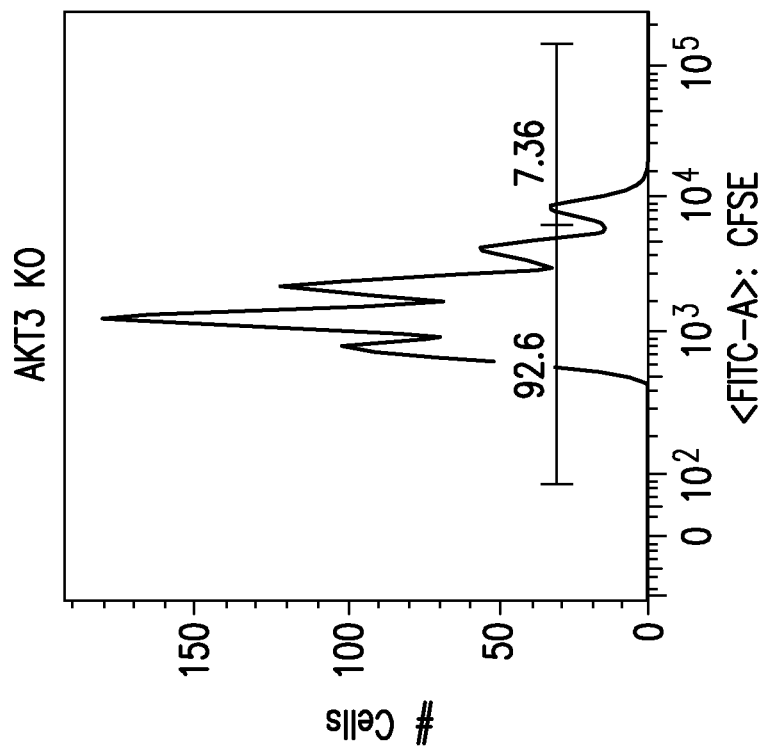
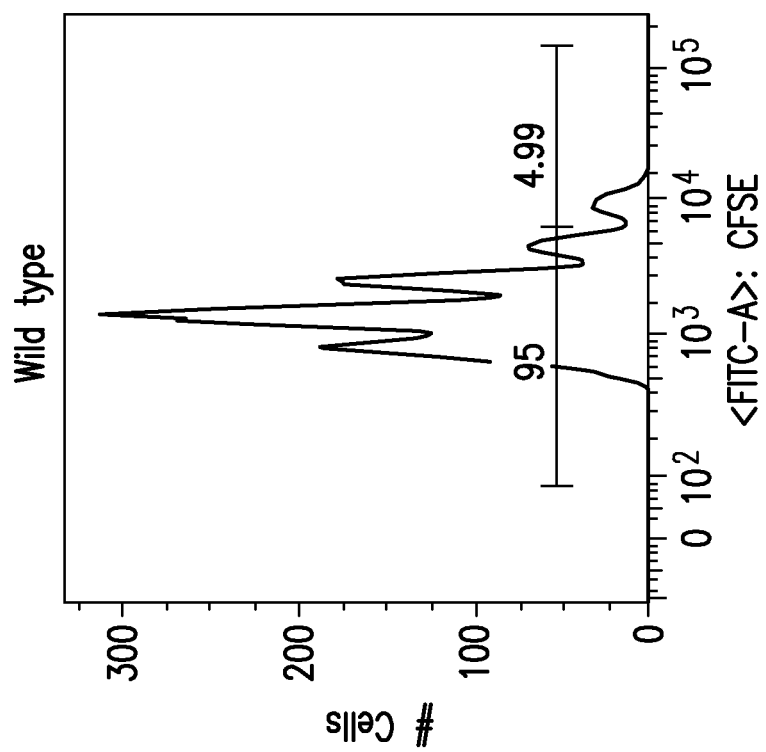
FIG. 15B
FIG. 15A

SEQUENCE LISTING

```
<160> NUMBER OF SEQ ID NOS: 14

<210> SEQ ID NO 1
<211> LENGTH: 1708
<212> TYPE: DNA
<213> ORGANISM: Homo sapiens

<400> SEQUENCE: 1 agggagtca  tcatgagcga  tgttaccatt  gtgaaggaag  gttgggttca  gaagagggga      60
gaatatataa  aaaactggag  gccaagatac  ttccttttga  agacagatgg  ctcattcata     120
ggatataaag  agaaacctca  agatgtggat  ttaccttatc  ccctcaacaa  cttttcagtg     180
gcaaaatgcc  agttaatgaa  aacagaacga  ccaaagccaa  acacatttat  aatcgatgt      240
```

```
ctccagtgga ctactgttat agagagaaca tttcatgtag atactccaga ggaaagggaa      300
gaatggacag aagctatcca ggctgtagca gacagactgc agaggcaaga agaggagaga      360
atgaattgta gtccaacttc acaaattgat aatataggag aggaagagat ggatgcctct      420
acaacccatc ataaaagaaa gacaatgaat gattttgact atttgaaact actaggtaaa      480
ggcacttttg ggaaagttat tttggttcga gagaaggcaa gtggaaaata ctatgctatg      540
aagattctga agaagaagt cattattgca aaggatgaag tggcacacac tctaactgaa       600
agcagagtat aaagaacac tagacatccc tttttaacat ccttgaaata ttccttccag       660
acaaaagacc gtttgtgttt tgtgatgaa tatgttaatg ggggcgagct gttttttccat      720 ttgtcgagag agcgggtgtt ctctgaggac cgcacacgtt tctatggtgc agaaattgtc      780
tctgccttgg actatctaca ttccggaaag attgtgtacc gtgatctcaa gttggagaat      840
ctaatgctgg acaaagatgg ccacataaaa attacagatt ttggactttg caagaaggg       900 atcacagatg cagccaccat gaagacattc tgtggcactc cagaatatct ggcaccagag      960
gtgttagaag ataatgacta tggccgagca gtagactggt ggggcctagg ggttgtcatg     1020
tatgaaatga tgtgtgggag gttacctttc tacaaccagg accatgagaa acttttttgaa    1080 ttaatattaa tggaagacat taaatttcct cgaacactct cttcagatgc aaaatcattg     1140
ctttcagggc tcttgataaa ggatccaaat aaacgcttg gtggaggacc agatgatgca      1200
aaagaaatta tgagacacag tttcttctct ggagtaaact ggcaagatgt atatgataaa     1260
aagcttgtac ctccttttaa acctcaagta acatctgaga cagatactag atattttgat     1320
gaagaattta cagctcagac tattacaata acaccacctg aaaaatatga tgaggatggt     1380
atggactgca tggacaatga gaggcggccg catttccctc aatttttccta ctctgcaagt    1440 ggacgagaat aagtctcttt cattctgcta cttcactgtc atcttcaatt tattactgaa     1500
aatgattcct ggacatcacc agtcctagct cttacacata gcaggggcac cttccgacat     1560
cccagaccag ccaagggtcc tcacccctcg ccacctttca ccctcatgaa aacacacata     1620
cacgcaaata cactccagtt tttgtttttg catgaaattg tatctcagtc taaggtctca     1680
tgctgttgct gctactgtct tactatta                                        1708

<210> SEQ ID NO 2
<211> LENGTH: 479
<212> TYPE: PRT
<213> ORGANISM: Homo sapiens

<400> SEQUENCE: 2

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110
```

Glu Glu Glu Arg Met Asn Cys Ser Pro Thr Ser Gln Ile Asp Asn Ile
            115                 120                 125

Gly Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
450                 455                 460

Arg Pro His Phe Pro Gln Phe Ser Tyr Ser Ala Ser Gly Arg Glu
465                 470                 475

<210> SEQ ID NO 3
<211> LENGTH: 478
<212> TYPE: PRT
<213> ORGANISM: Homo sapiens

<400> SEQUENCE: 3

Ser Asp Val Thr Ile Val Lys Glu Gly Trp Val Gln Lys Arg Gly Glu

```
1               5                   10                  15
Tyr Ile Lys Asn Trp Arg Pro Arg Tyr Phe Leu Leu Lys Thr Asp Gly
                20                  25                  30

Ser Phe Ile Gly Tyr Lys Glu Lys Pro Gln Asp Val Asp Leu Pro Tyr
            35                  40                  45

Pro Leu Asn Asn Phe Ser Val Ala Lys Cys Gln Leu Met Lys Thr Glu
        50                  55                  60

Arg Pro Lys Pro Asn Thr Phe Ile Ile Arg Cys Leu Gln Trp Thr Thr
65                  70                  75                  80

Val Ile Glu Arg Thr Phe His Val Asp Thr Pro Glu Glu Arg Glu Glu
                85                  90                  95

Trp Thr Glu Ala Ile Gln Ala Val Ala Asp Arg Leu Gln Arg Gln Glu
            100                 105                 110

Glu Glu Arg Met Asn Cys Ser Pro Thr Ser Gln Ile Asp Asn Ile Gly
        115                 120                 125

Glu Glu Glu Met Asp Ala Ser Thr Thr His His Lys Arg Lys Thr Met
130                 135                 140

Asn Asp Phe Asp Tyr Leu Lys Leu Leu Gly Lys Gly Thr Phe Gly Lys
145                 150                 155                 160

Val Ile Leu Val Arg Glu Lys Ala Ser Gly Lys Tyr Tyr Ala Met Lys
                165                 170                 175

Ile Leu Lys Lys Glu Val Ile Ile Ala Lys Asp Glu Val Ala His Thr
            180                 185                 190

Leu Thr Glu Ser Arg Val Leu Lys Asn Thr Arg His Pro Phe Leu Thr
        195                 200                 205

Ser Leu Lys Tyr Ser Phe Gln Thr Lys Asp Arg Leu Cys Phe Val Met
210                 215                 220

Glu Tyr Val Asn Gly Gly Glu Leu Phe Phe His Leu Ser Arg Glu Arg
225                 230                 235                 240

Val Phe Ser Glu Asp Arg Thr Arg Phe Tyr Gly Ala Glu Ile Val Ser
                245                 250                 255

Ala Leu Asp Tyr Leu His Ser Gly Lys Ile Val Tyr Arg Asp Leu Lys
            260                 265                 270

Leu Glu Asn Leu Met Leu Asp Lys Asp Gly His Ile Lys Ile Thr Asp
        275                 280                 285

Phe Gly Leu Cys Lys Glu Gly Ile Thr Asp Ala Ala Thr Met Lys Thr
290                 295                 300

Phe Cys Gly Thr Pro Glu Tyr Leu Ala Pro Glu Val Leu Glu Asp Asn
305                 310                 315                 320

Asp Tyr Gly Arg Ala Val Asp Trp Trp Gly Leu Gly Val Val Met Tyr
                325                 330                 335

Glu Met Met Cys Gly Arg Leu Pro Phe Tyr Asn Gln Asp His Glu Lys
            340                 345                 350

Leu Phe Glu Leu Ile Leu Met Glu Asp Ile Lys Phe Pro Arg Thr Leu
        355                 360                 365

Ser Ser Asp Ala Lys Ser Leu Leu Ser Gly Leu Leu Ile Lys Asp Pro
370                 375                 380

Asn Lys Arg Leu Gly Gly Gly Pro Asp Asp Ala Lys Glu Ile Met Arg
385                 390                 395                 400

His Ser Phe Phe Ser Gly Val Asn Trp Gln Asp Val Tyr Asp Lys Lys
                405                 410                 415

Leu Val Pro Pro Phe Lys Pro Gln Val Thr Ser Glu Thr Asp Thr Arg
            420                 425                 430
```

```
Tyr Phe Asp Glu Glu Phe Thr Ala Gln Thr Ile Thr Ile Thr Pro Pro
        435                 440                 445
Glu Lys Tyr Asp Glu Asp Gly Met Asp Cys Met Asp Asn Glu Arg Arg
    450                 455                 460
Pro His Phe Pro Gln Phe Ser Tyr Ser Ala Ser Gly Arg Glu
465                 470                 475

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Arg Arg Arg Arg Arg Arg Arg
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Arg Arg Gln Arg Arg Thr Ser Lys Leu Met Lys Arg
1               5                   10

<210> SEQ ID NO 6
<211> LENGTH: 27
<212> TYPE: PRT
<213> ORGANISM: Artificial Sequence
<220> FEATURE:
<223> OTHER INFORMATION: Synthetic peptide

<400> SEQUENCE: 6

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
            20                  25

<210> SEQ ID NO 7
<211> LENGTH: 33
<212> TYPE: PRT
<213> ORGANISM: Artificial Sequence
<220> FEATURE:
<223> OTHER INFORMATION: Synthetic peptide

<400> SEQUENCE: 7

Lys Ala Leu Ala Trp Glu Ala Lys Leu Ala Lys Ala Leu Ala Lys Ala
1               5                   10                  15
Leu Ala Lys His Leu Ala Lys Ala Leu Ala Lys Ala Leu Lys Cys Glu
            20                  25                  30
Ala

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8
```

Arg Gln Ile Lys Ile Trp Phe Gln Asn Arg Arg Met Lys Trp Lys Lys
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: Synthetic linker

<400> SEQUENCE: 9

Gly Ser Gly Ser Gly Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic linker

<400> SEQUENCE: 10

Ala Ser Gly Gly Gly Ser
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic linker

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 20
<212> TYPE: PRT
<213> ORGANISM: Artificial Sequence
<220> FEATURE:
<223> OTHER INFORMATION: Synthetic linker

<400> SEQUENCE: 12

Gly Gly Gly Gly Ser Gly Gly Gly Gly Ser Gly Gly Gly Gly Ser Gly
1               5                   10                  15

Gly Gly Gly Ser
            20

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Tyr Gly Arg Lys Lys Arg Arg Gln Arg Arg Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 14

Arg Lys Lys Arg Arg Gln Arg Arg Arg
1               5
```

METHODS OF MODULATING IMMUNE RESPONSES BY MODIFYING AKT3 BIOACTIVITY

CROSS-REFERENCE TO RELATED APPLICATIONS

This application claims benefit of and priority to U.S. Provisional Application No. 61/980,795, filed on Apr. 17, 2014, and which is incorporated by reference in its entity.

REFERENCE TO SEQUENCE LISTING

The Sequence Listing submitted Apr. 17, 2015 as a text file named "GRU_2014_020_ST25.txt," created on Apr. 17, 2015, and having a size of 14,000 bytes is hereby incorporated by reference pursuant to 37 C.F.R. §1.52(e)(5).

FIELD OF THE INVENTION

The invention is generally directed to compositions for modulating Akt3 activity, and methods of use thereof for modulating regulator T cells.

BACKGROUND OF THE INVENTION

Regulatory T cells (Tregs) are a subset of CD4+ T cells that suppress immune responses and are essential mediators of self-tolerance and immune homeostasis (Sakaguchi, et al., *Cell*, 133, 775-787 (2008)). Depletion or inactivation of Tregs results in the development of severe autoimmunity (Sakaguchi, et al., *J. Immunol.*, 155, 1151-1164 (1995)), and their accumulation inhibits anti-tumor immunity (Dannull, et al., *The Journal of clinical investigation*, 115, 3623-3633 (2005)). Tregs are characterized by Foxp3 expression, a transcription factor belonging to the Forkehead Box family of transcription factors. The Foxp3 is a master regulator of Tregs, as it is necessary for their development and function (Hori, *Science*, 299, 1057-1061 (2003); Fontenot, et al., *Nat Immunol.*, 4(4):330-6 (2003). Epub 2003 Mar. 3; Khattri, et al., *Nat Immunol.*, 4(4):337-42 (2003). Epub 2003 Mar. 3)).

There are two major types of Tregs: thymus-derived Tregs (or natural Tregs (nTregs)) that constitute 5-10% of the total peripheral CD4+ T cells, and peripheral TGFβ-induced Tregs (iTregs). Both types are shown to have immunosuppressive properties mediated via several processes that involve immunosuppressive soluble factors or cell contact (Bluestone, et al., *Nat Rev Immunol*, 3, 253-257 (2003); Glisic, et al., *Cell and Tissue Research*, 339, 585-595 (2010); Hori, *Science*, 299, 1057-1061 (2003); Sakaguchi, *Cell*, 101, 455-458 (2000); Sakagushi, et al., *Curr. Top Microbiol. Immunol.*, 305, 51-66 (2006); Sakagushi, et al., *Immunol., Rev.*, 212, 8-27 (2006); (Schmidt, et al., *Front Immunol.*, 3:51 (2012)). However, the molecular mechanisms by which nTreg and iTreg develop and then exhibit non-redundant roles to suppress the immunity are not fully understood (Dipica, et al., *Immunity*, 35(1):109-122 (2011)).

PI3K-Akt signaling affects many processes and is central to many signaling pathways. Akt phosphorylation and kinase activity are induced by PI3K activation, which is, in turn, induced by several growth factor receptors, TCR, CD28, and IL-2R, among many others (Parry, et al., *Trends in Immunology*, 28, 161-168 (2007)). In mammals, there are three Akt isoforms, namely Akt1, Akt2, and Akt3, encoded by three independent genes. In vitro, these isoforms appear to have redundant functions, as different extracellular inputs can induce similar Akt signaling patterns (Franke, Science 1, pe29-(2008)). However, isoform-specific knockouts show unique features and their involvement in diseases and physiological conditions is different (Boland, et al., *American Journal of Human Genetics*, 81, 292-303 (2007); DeBosch, et al., *J. Biol. Chem*, 281, 32841-32851 (2006); Emamian, et al., *Nat Genet*, 36, 131-137 (2004); Garofalo, et al., *The Journal of clinical investigation*, 112, 197-208 (2003); George, et al., *Science*, 304, 1325-1328 (2004); Nakatani, et al., *The Journal of Biological Chemistry*, 274, 21528-21532 (1999); Tschopp, et al., *Development* (Cambridge, England), 132, 2943-2954 (2005); Yang, et al., *J. Biol. Chem.*, 278, 32124-32131 (2003)).

Studies have shown that Akt1 and Akt2 can negatively regulate the transcriptional signature of Treg, thereby selectively affecting Treg lineage differentiation (Sauer, et al., *Proceedings of the National Academy of Sciences*, 105, 7797-7802 (2008a)). Additionally, although it was shown that inhibition of Akt1 and Akt2 isoforms increase Foxp3 expression in TGFβ induced iTregs (Sauer, et al., *Proc. Natl. Acad. Sci. USA*, 105, 7797-7802 (2008b)), the mechanism remained unclear. Another finding shows that deletion of Akt2 resulted in defective iTh17 cell differentiation but preserved nTh17 cell development (Kim, et al., *Nat Immunol.*, 14(6):611-8 (2013) Epub 2013 May 5). Further, Akt3 is also expressed in immune cells and the spinal cord of Akt3 knockout mice have decreased numbers of Foxp3+ regulatory T cells compared with wild type mice (Tsiperson, et al., *J Immunol.*, 190(4):1528-39 (2013) Epub 2013 Jan. 18)). Thus, although some studies have examined the relevance of Akt isoform expression on T cell biology (Carson, et al., *Annals of the New York Academy of Sciences*, 1103, 167-178 (2007), Crellin, et al., *Blood*, 109, 2014-2022 (2007a); Crellin, et al., *Journal of Immunological Methods*, 324, 92-104 (2007b); Haxhinasto, *J. Exp. Med.*, 205, 565-574 (2008); Li, et al., *Blood*, 106, 3068-3073 (2005); Patton, et al., *Biochem. Soc. Trans.*, 35, 167-171 (2007); Patton, et al., *J. Immunology* 177, 6598-6602 (2006); Sauer, et al., *Proc. Natl. Acad. Sci. USA*, 105, 7797-7802 (2008b); Walsh, et al., *J. Clin. Invest.*, 116, 2521-2531. (2006)), the roles that Akt isoforms play in Treg function and induction was not clear.

Therefore, there remains a need to identify the molecular pathways underlying Treg activity, and to develop therapeutics for targeting the pathways to modulate Treg activity.

It is an object of the invention to provide a molecular pathway for modulating the development of nTregs and the polarization of iTregs, and to provide compositions for modulating the pathway.

It is an object of the invention to provide methods of using the compositions to modulate nTregs and iTregs in subjects in need therefore.

SUMMARY OF THE INVENTION

It has been discovered that Akt3 modulates the suppressive function of natural Treg and the polarization of induced Treg. Therefore, methods of modulating immune responses by modulating Akt3 bioavailability are provided.

For example, methods of decreasing an immune suppressive response, increasing an immune stimulating response, or a combination thereof in a subject in need thereof are disclosed. The methods typically include administering the subject a composition including a compound that reduces the bioavailability of Akt3 in an amount effective to reduce the immune suppressive response, increase the immune stimulating response, or a combination thereof in the subject.

In some embodiments the immune suppressive response that is reduced is selected from the group consisting of an immune suppressive function of natural Treg (nTreg) and induction of conventional T cells into induced Treg (iTreg). The immune suppressive function of nTreg can be the secretion of one or more anti-inflammatory cytokines. The anti-inflammatory cytokine(s) can IL10, TGFβ, or a combination thereof.

In some embodiments, the subject has cancer or an infection. Therefore, methods of treating cancers and infections by administering a subject in need thereof an effective amount of a compound that reduces the bioavailability of Akt3 are also disclosed. Exemplary cancers that can be treated include, but are not limited to, bladder, brain, breast, cervical, colo-rectal, esophageal, kidney, liver, lung, nasopharangeal, pancreatic, prostate, skin, stomach, uterine, ovarian, testicular and hematologic cancers. Exemplary infectious diseases that can be treated include, but are not limited to, those caused by a bacterium, virus, protozoan, helminth, or other microbial pathogen.

Exemplary compounds that reduce the bioavailability of Akt3 are also provided, and include, but are not limited to, inhibitory Akt3 polypeptides that bind to one or more substrates of Akt3 and prevent binding to Akt3; small molecules that bind to and inhibit occupancy or activity of the Akt3 kinase domain; substrate mimics that bind to Akt3 and serves as a molecular sink for Akt3 kinase activity; and inhibitory nucleic acids that reduce expression of Akt3.

Methods of increasing an immune suppressive response, decreasing an immune stimulating response, or a combination thereof in a subject in need thereof are also disclosed. The methods typically include administering the subject a composition including a compound that increases the bioavailability of Akt3 in an amount effective to increase the immune suppressive response, decrease the immune stimulating response, or a combination thereof in the subject.

In some embodiments the immune suppressive response that is increased is selected from the group consisting of an immune suppressive function of natural Treg (nTreg) and induction of conventional T cells into induced Treg (iTreg). The immune suppressive function of nTreg can be the secretion of one or more anti-inflammatory cytokines. The anti-inflammatory cytokine(s) can IL10, TGFβ, or a combination thereof.

In some embodiments, the subject has an autoimmune or inflammatory disease or disorder; has a transplanted tissue or organ; or has graft verse host disease (GVD). Therefore, methods for treating autoimmune or inflammatory diseases or disorders, treating graft verse host disease (GVD), and reducing rejection of a transplanted tissue or organ are also provided.

Exemplary compounds that increase the bioavailability of Akt3 are also provided, and include, but are not limited to, functional Akt3 polypeptides, functional variants, or functional fusion proteins thereof; nucleic acids encoding functional Akt3 polypeptides, functional variants, or functional fusion proteins thereof; transcription factors of Akt3; and nucleic acids encoding transcription factors of Akt3.

Combination therapies and vaccine formulations including modulators of Akt3 bioactivity and methods of use thereof are also provided.

BRIEF DESCRIPTION OF THE DRAWINGS

FIGS. 3A-3D are single parameter histograms showing expression of cell surface markers GITR (3A), CTLA4 (3B), PD1 (3C) and CD25 (3D) on Tregs isolated from wildtype and Akt3 knockout mice and analyzed by flow cytometry.

FIGS. 15A-15B are single parameter histograms showing proliferation of iTregs by flow cytomeric analysis of CD4+CD25− naïve T cells enriched from total splenocytes from wildtype (15A) and Akt3 knockout (15B) mice and stimulated in vitro with plate bound anti-CD3, soluble anti-CD28, and IL-2 in the presence of TGFβ (iTreg condition) for 72 h. iTreg phenotype was assess in iTreg (gated on CD4+Foxp3+) cells from Akt3 knockout compare to that of wild type.

DETAILED DESCRIPTION OF THE INVENTION

I. Definitions

Figure 1A:
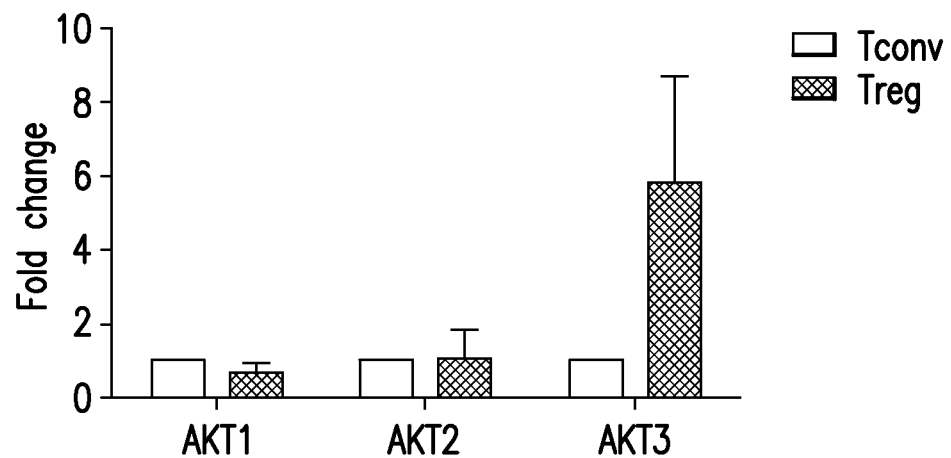
FIG. 1A is a bar graph showing the fold change in Akt1, Akt2, and Akt3 protein levels as determined by densitometry following western blots analysis of lysates of CD4+CD25− convention T cells (Tconv) and CD4+CD25+ regulatory T cells (Treg) enriched from total splenocytes and stimulated with anti-CD3, anti-CD28 and IL-2 for 72 hours (normalized to β-actin protein levels, n=3, *p<0.05).

The term "stimulate expression of" means to affect expression of, for example to induce expression or activity, or induce increased/greater expression or activity relative to normal, healthy controls.

The terms "immune activating response", "activating immune response", and "immune stimulating response" refer to a response that initiates, induces, enhances, or increases the activation or efficiency of innate or adaptive immunity. Such immune responses include, for example, the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response can also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

The terms "suppressive immune response" and "immune suppressive response" refer to a response that reduces or prevents the activation or efficiency of innate or adaptive immunity.

The term "immune tolerance" as used herein refers to any mechanism by which a potentially injurious immune response is prevented, suppressed, or shifted to a non-injurious immune response (Bach, et al., *N. Eng. J. Med.*, 347:911-920 (2002)).

The term "tolerizing vaccine" as used herein is typically an antigen-specific therapy used to attenuate autoreactive T and/or B cell responses, while leaving global immune function intact.

An "immunogenic agent" or "immunogen" is capable of inducing an immunological response against itself on administration to a mammal, optionally in conjunction with an adjuvant.

The term "immune cell" refers to cells of the innate and acquired immune system including neutrophils, eosinophils, basophils, monocytes, macrophages, dendritic cells, lymphocytes including B cells, T cells, and natural killer cells.

As used herein "conventional T cells" are T lymphocytes that express an αβ T cell receptor (TCR) as well as a co-receptor CD4 or CD8. Conventional T cells are present in the peripheral blood, lymph nodes, and tissues. See, Roberts and Girardi, "Conventional and Unconventional T Cells", *Clinical and Basic Immunodermatology*, pp. 85-104, (Gaspari and Tyring (ed.)), Springer London (2008).

As used herein "unconventional T cells" are lymphocytes that express a γδ TCR and may commonly reside in an epithelial environment such as the skin, gastrointestinal tract, or genitourinary tract. Another subset of unconventional T cells is the invariant natural killer T (NKT) cell, which has phenotypic and functional capacities of a conventional T cell, as well as features of natural killer cells (e.g., cytolytic activity). See, Roberts and Girardi, "Conventional and Unconventional T Cells", *Clinical and Basic Immunodermatology*, pp. 85-104, (Gaspari and Tyring (ed.)), Springer London (2008).

As used herein "Treg" refers to a regulatory T cell or cells. Regulatory T cells are a subpopulation of T cells which modulate the immune system, maintain tolerance to self-antigens, abrogate autoimmune disease, and otherwise suppress immune stimulating or activating responses of other cells. Regulatory T cells come in many forms with the most well-understood being those that express CD4, CD25, and Foxp3.

As used herein "natural Treg" or "nTreg" refers to a regulatory T cell or cells that develop in the thymus.

As used herein "induced Treg" or "iTreg" refers to a regulatory T cell or cells that develop from mature CD4+ conventional T cells outside of the thymus.

The "bioactivity" of Akt3 refers to the biological function of the Akt3 polypeptide. Bioactivity can be increased or reduced by increasing or reducing the activity of basal levels of polypeptide, increasing or reducing the avidity of basal levels of polypeptide, the quantity of the polypeptide, the ratio of Akt3 relative to one or more other isoforms of Akt (e.g., Akt1 or Akt2) of the polypeptide, increasing or reducing the expression levels of the polypeptide (including by increasing or decreasing mRNA expression of Akt3), or a combination thereof. For example, bioavailable Akt3 polypeptide is a polypeptide that has kinase activity and can bind to and phosphorylate a substrate of Akt3. Akt3 polypeptide that is not bioavailable includes Akt3 polypeptide that is mis-localized or in-capable of binding to and phosphorylating Akt substrates.

As used herein, the phrase that a molecule "specifically binds" or "displays specific binding" to a target refers to a binding reaction which is determinative of the presence of the molecule in the presence of a heterogeneous population of other biologics.

Under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The terms "oligonucleotide" and "polynucleotide" generally refer to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 mg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Third Edition, Cold Spring Harbor, N.Y. (2000).

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, the term "host cell" refers to prokaryotic and eukaryotic cells into which a recombinant nucleotide, such as a vector, can be introduced.

As used herein, "transformed" and "transfected" encompass the introduction of a nucleic acid (e.g. a vector) into a cell by a number of techniques known in the art.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutammine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign® (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

"Protein Transduction Domain" or PTD refers to a polypeptide, polynucleotide, carbohydrate, or organic or inorganic compounds that facilitate traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include, but are not limited to, HIV TAT YGRKKRRQRRR (SEQ ID NO:13) or RKKRRQRRR (SEQ ID NO:14); 11 Arginine residues, or positively charged polypeptides or polynucleotides having 8-15 residues, preferably 9-11 residues.

The term "carrier" refers to an organic or inorganic ingredient, natural or synthetic, with which the active ingredient is combined to facilitate the application.

The term "pharmaceutically acceptable" means a non-toxic material that does not interfere with the effectiveness of the biological activity of the active ingredients.

The term "pharmaceutically-acceptable carrier" means one or more compatible solid or liquid fillers, diluents or encapsulating substances which are suitable for administration to a human or other vertebrate animal.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "individual," "subject," and "patient" are used interchangeably herein, and refer to a mammal, including, but not limited to, humans, rodents, such as mice and rats, and other laboratory animals.

II. Compositions for Use in Methods Modulating Akt3

It has been discovered that Akt3 is the dominant Akt isoform that regulates the function and induction in natural and induced Treg. The Examples below illustrate that loss of Akt3 in nTreg reduces expression of IL-10 and TGFβ inhibitory cytokines and leads to an overall reduction in the suppressive ability of the cells. In contrast, loss of Akt3 reduces the induction level, but not suppressive function of iTreg. Accordingly, compositions for modulating Akt3 expression in regulatory T cells, and methods of use thereof are disclosed.

The compositions for modulating Akt3 include one or more compounds that increase or decrease the bioavailability of Akt3. Akt3, also referred to as RAC-gamma serine/threonine-protein kinase is an enzyme that in humans is encoded by the Akt3 gene. Akt kinases are known to be regulators of cell signaling in response to insulin and growth factors and are associated with a broad range of biological processes including cell proliferation, differentiation, apoptosis, tumorigenesis, as well as glycogen synthesis and glucose uptake. Akt3 has been shown to be stimulated by platelet-derived growth factor (PDGF), insulin, and insulin-like growth factor 1 (IGF1).

A. Compositions for Increasing the Bioactivity of Akt3

Compositions including one or more compounds for increasing the bioactivity of Akt3 are disclosed. In some embodiments, the compound is Akt3 polypeptide, a fusion protein including an Akt3 polypeptide, an isolated nucleic acid encoding a Akt3 polypeptide or Akt3 fusion protein, or an agent such as a transcription factor that increases endogenous expression of an Akt3 polypeptide. Up regulation of Akt3 can increase, or prevent the reduction of, expression of IL-10 and TGFβ inhibitory cytokines in nTreg and increase, or prevent a reduction in, the overall suppressive ability of the cells. Up regulation of Akt3 in conventional T cells can increase, or prevent a reduction in, the induction level iTreg.

1. Akt3 Polypeptides

In some embodiments a composition for increasing the bioactivity of Akt3 includes an Akt3 polypeptide. Akt3 kinase activity mediates serine and/or threonine phosphorylation of a range of downstream substrates. Nucleic acid sequences for Akt3 are known in the art. See, for example, Genbank accession no. AF124141.1: *Homo sapiens* protein kinase B gamma mRNA, complete cds, which is specifically incorporated by references in its entirety, and provides the nucleic acid sequence:

```
(SEQ ID NO: 1)
AGGGGAGTCATCATGAGCGATGTTACCATTGTGAAGGAAGGTTGGGTTCA

GAAGAGGGGAGAATATATAAAAAACTGGAGGCCAAGATACTTCCTTTTGA

AGACAGATGGCTCATTCATAGGATATAAAGAGAAACCTCAAGATGTGGAT

TTACCTTATCCCCTCAACAACTTTTCAGTGGCAAAATGCCAGTTAATGAA

AACAGAACGACCAAAGCCAAACACATTTATAATCAGATGTCTCCAGTGGA

CTACTGTTATAGAGAGAACATTTCATGTAGATACTCCAGAGGAAAGGGAA

GAATGGACAGAAGCTATCCAGGCTGTAGCAGACAGACTGCAGAGGCAAGA

AGAGGAGAGAATGAATTGTAGTCCAACTTCACAAATTGATAATATAGGAG

AGGAAGAGATGGATGCCTCTACAACCCATCATAAAAGAAAGACAATGAAT

GATTTTGACTATTTGAAACTACTAGGTAAAGGCACTTTTGGGAAAGTTAT

TTTGGTTCGAGAGAAGGCAAGTGGAAAATACTATGCTATGAAGATTCTGA

AGAAAGAAGTCATTATTGCAAAGGATGAAGTGGCACACACTCTAACTGAA

AGCAGAGTATTAAAGAACACTAGACATCCCTTTTTAACATCCTTGAAATA

TTCCTTCCAGACAAAAGACCGTTTGTGTTTTGTGATGGAATATGTTAATG

GGGGCGAGCTGTTTTTCCATTTGTCGAGAGAGCGGGTGTTCTCTGAGGAC

CGCACACGTTTCTATGGTGCAGAAATTGTCTCTGCCTTGGACTATCTACA

TTCCGGAAAGATTGTGTACCGTGATCTCAAGTTGGAGAATCTAATGCTGG

ACAAAGATGGCCACATAAAAATTACAGATTTTGGACTTTGCAAAGAAGGG

ATCACAGATGCAGCCACCATGAAGACATTCTGTGGCACTCCAGAATATCT

GGCACCAGAGGTGTTAGAAGATAATGACTATGGCCGAGCAGTAGACTGGT

GGGGCCTAGGGGTTGTCATGTATGAAATGATGTGTGGGAGGTTACCTTTC

TACAACCAGGACCATGAGAAACTTTTTGAATTAATATTAATGGAAGACAT

TAAATTTCCTCGAACACTCTCTTCAGATGCAAAATCATTGCTTTCAGGGC

TCTTGATAAAGGATCCAAATAAACGCCTTGGTGGAGGACCAGATGATGCA

AAAGAAATTATGAGACACAGTTTCTTCTCTGGAGTAAACTGGCAAGATGT

ATATGATAAAAAGCTTGTACCTCCTTTTAAACCTCAAGTAACATCTGAGA

CAGATACTAGATATTTTGATGAAGAATTTACAGCTCAGACTATTACAATA

ACACCACCTGAAAAATATGATGAGGATGGTATGGACTGCATGGACAATGA

GAGGCGGCCGCATTTCCCTCAATTTTCCTACTCTGCAAGTGGACGAGAAT

AAGTCTCTTTCATTCTGCTACTTCACTGTCATCTTCAATTTATTACTGAA

AATGATTCCTGGACATCACCAGTCCTAGCTCTTACACATAGCAGGGGCAC
```

-continued

CTTCCGACATCCCAGACCAGCCAAGGGTCCTCACCCCTCGCCACCTTTCA

CCCTCATGAAAACACACATACACGCAAATACACTCCAGTTTTTGTTTTTG

CATGAAATTGTATCTCAGTCTAAGGTCTCATGCTGTTGCTGCTACTGTCT

TACTATTA.

Amino acid sequences are also known in the art. See, for example, UniProtKB/Swiss-Prot accession no. Q9Y243 (Akt3_HUMAN), which is specifically incorporated by reference in its entirety and provides the amino acid sequence:

(SEQ ID NO: 2)
MSDVTIVKEGWVQKRGEYIKNWRPRYFLLKTDGSFIGYKEKPQDVDLPYP

LNNFSVAKCQLMKTERPKPNTFIIRCLQWTTVIERTFHVDTPEEREENTE

ATQAVADRLQRQEEERMNCSPTSQIDNIGEEEMDASTTHHKRKTMNDFDY

LKLLGKGTFGKVILVREKASGKYYAMKILKKEVIIAKDEVAHTLTESRVL

KNTRHPFLTSLKYSFQTKDRLCFVMEYVNGGELFFHLSRERVFSEDRTRF

YGAEIVSALDYLHSGKIVYRDLKLENLMLDKDGHIKITDFGLCKEGITDA

ATMKTFCGTPEYLAPEVLEDNDYGRAVDWWGLGVVMYEMMCGRLPFYNQD

HEKLFELILMEDIKFPRTLSSDAKSLLSGLLIKDPNKRLGGGPDDAKEIM

RHSFFSGVNWQDVYDKKLVPPFKPQVTSETDTRYFDEEFTAQTITITPPE

KYDEDGMDCMDNERRPHFPQFSYSASGRE.

The domain structure of Akt3 is reviewed in Romano, *Scientifica*, Volume 2013 (2013), Article ID 317186, 12 pages, and includes an N-terminal pleckstrin homology domain (PH), followed by a catalytic kinase domain (KD), and the C-terminal regulatory hydrophobic region. The catalytic and regulatory domains are both important for the biological actions mediated by Akt protein kinases and exhibit the maximum degree of homology among the three Akt isoforms. The PH domain binds lipid substrates, such as phosphatidylinositol (3,4) diphosphate (PIP2) and phosphatidylinositol (3,4,5) triphosphate (PIP3). The ATP binding site is situated approximately in the middle of the catalytic kinase domain, which has a substantial degree of homology with the other components of the AGCkinases family, such as p70 S6 kinase (S6K) and p90 ribosomal S6 kinase (RSK), protein kinase A (PKA) and protein kinase B (PKB). The hydrophobic regulatory moiety is a typical feature of the AGC kinases family. With reference to SEQ ID NO:2, Akt 3 is generally considered to have the following molecule processing and domain structure outlined below.

Molecule Processing:

| Feature key | Position(s) | Length | Description |
| --- | --- | --- | --- |
| Initiator methionine | 1 | 1 | Removed |
| Chain | 2-479 | 478 | Akt3 |

Regions:

| Feature key | Position(s) | Length | Description |
| --- | --- | --- | --- |
| Domain | 5-107 | 103 | PH |
| Domain | 148-405 | 258 | Protein kinase |

| Feature key | Position(s) | Length | Description |
| --- | --- | --- | --- |
| Domain | 406-479 | 74 | AGC-kinase C-terminal |
| Nucleotide binding | 154-162 | 9 | ATP |

Sites:

| Feature key | Position(s) | Length | Description |
| --- | --- | --- | --- |
| Active site | 271 | 1 | Proton acceptor |
| Binding site | 177 | 1 | ATP |

The initiator methionine of SEQ ID NO:2 is disposable for Akt3 function. Therefore, in some embodiments, the compound that increases the bioavailability of Akt3 has the amino acid sequence (SEQ ID NO: 3)
SDVTIVKEGWVQKRGEYIKNWRPRYFLLKTDGSFIGYKEKPQDVDLPYPL

NNFSVAKCQLMKTERPKPNTFIIRCLQWTTVIERTFHVDTPEEREENTEA

TQAVADRLQRQEEERMNCSPTSQIDNIGEEEMDASTTHHKRKTMNDFDYL

KLLGKGTFGKVILVREKASGKYYAMKILKKEVIIAKDEVAHTLTESRVLK

NTRHPFLTSLKYSFQTKDRLCFVMEYVNGGELFFHLSRERVFSEDRTRFY

GAEIVSALDYLHSGKIVYRDLKLENLMLDKDGHIKITDFGLCKEGITDAA

TMKTFCGTPEYLAPEVLEDNDYGRAVDWWGLGVVMYEMMCGRLPFYNQDH

EKLFELILMEDIKFPRTLSSDAKSLLSGLLIKDPNKRLGGGPDDAKEIMR

HSFFSGVNWQDVYDKKLVPPFKPQVTSETDTRYFDEEFTAQTITITPPEK

YDEDGMDCMDNERRPHFPQFSYSASGRE.

Two specific sites, one in the kinase domain (Thr-305 with reference to SEQ ID NO:2) and the other in the C-terminal regulatory region (Ser-472 with reference to SEQ ID NO:2), need to be phosphorylated for full activation of Akt3. Interaction between the PH domain of Akt3 and TCL1A enhances Akt3 phosphorylation and activation. IGF-1 leads to the activation of Akt3, which may play a role in regulating cell survival.

A composition for increasing the bioavailability of Akt3 can include a polypeptide having SEQ ID NO:2 or SEQ ID NO:3, or a sequence having at least 80%, 85%, 90%, 95%, 99%, or 100% sequence identity to SEQ ID NO:2 or SEQ ID NO:3, or a fragment or variant of SEQ ID NO:2 or SEQ ID NO:3.

A number of naturally occurring variants and their activities are known in the art, and include, but are not limited to, those described in UniProtKB/Swiss-Prot accession no. Q9Y243 (Akt3_HUMAN). Variants and fragments of Akt3 that are useful for increasing the bioavailability of Akt3 typically include the amino acids (e.g., Thr-305 and Ser-472 with reference to SEQ ID NO:2, or the corresponding residue in other sequences) more preferably the domain or domains of Akt3 needed for binding to and phosphorylating substrates of Akt3 (e.g., the protein kinase domain, and preferably one or more of the PH domain, the AGC-kinase C-terminal, and the ATP domain). Useful variants and fragments include those that increase biological activity as indicated by any of the assays described herein, or that increase half-life or stability of the protein. The Akt3 polypeptides and fragments and variants thereof as well as fusion proteins thereof, having Akt3 activity can be engineered to increase biological activity. In a preferred embodiment, the Akt3 polypeptide or fusion protein is modified with at least one amino acid substitution, deletion, or insertion that increases the binding of the molecule to an Akt3 substrate. Other variants of Akt3 can be engineered to have increased kinase activity.

Variant Akt3 polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art. The variants can be modified to adjust for effects of the half-life of Akt3 polypeptides, fragments, or fusions thereof at serum and endosomal pH.

2. Akt3 Fusion Proteins

Fusion proteins containing one or more of the Akt3 polypeptides disclosed above can be coupled to other polypeptides to form fusion proteins. Atk3 fusion polypeptides have a first fusion partner including all or a part of a Akt3 protein fused (i) directly to a second polypeptide or, (ii) optionally, fused to a linker peptide sequence that is fused to the second polypeptide. The peptide/polypeptide linker domain can either be a separate domain, or alternatively can be contained within one of the other domains (Akt3 polypeptide or second polypeptide) of the fusion protein.

Fusion proteins can have formula I:

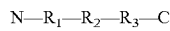

wherein "N" represents the N-terminus of the fusion protein, "C" represents the C-terminus of the fusion protein, "$R_1$" is a Akt3 polypeptide, or functional variant or fragment thereof, "$R_2$" is an optional peptide/polypeptide linker domain, and "$R_3$" is a second polypeptide. Alternatively, $R_3$ is the Akt3 polypeptide, or functional variant or fragment thereof and $R_1$ is the second polypeptide.

a. Second Polypeptide

The Akt3 polypeptide can be fused to a second polypeptide. The presence of the second polypeptide can alter the solubility, stability, affinity and/or valency of the Akt3 fusion polypeptide. As used herein, "valency" refers to the number of binding sites available per molecule. In one embodiment the second polypeptide is a polypeptide from a different source or different protein.

i. Protein Transduction Domains

In some embodiments, the Akt3 fusion proteins include one or more domains for enhancing delivery of the polypeptide across the plasma membrane in into the interior of cells. The Akt3 fusion proteins can be modified to include a protein transduction domain (PTD), also known as cell penetrating peptides (CPPS). PTDs are known in the art, and include, but are not limited to, small regions of proteins that are able to cross a cell membrane in a receptor-independent mechanism (Kabouridis, P., *Trends in Biotechnology* (11): 498-503 (2003)). Although several of PTDs have been documented, the two most commonly employed PTDs are derived from TAT (Frankel and Pabo, *Cell*, 55(6):1189-93 (1988)) protein of HIV and Antennapedia transcription factor from *Drosophila*, whose PTD is known as Penetratin (Derossi et al., *J. Biol. Chem.*, 269(14):10444-50 (1994)).

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ ID NO:13)) of the parent protein that appears to be critical for uptake. Additionally, the basic domain Tat(49-57) or RKKRRQRRR (SEQ ID NO:14) has been shown to be a PTD. TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al., *Proc. Natl. Acad. Sci. USA.*, 97(24): 13003-8 (2000)) to up to 33 fold in mammalian cells. (Ho et al., *Cancer Res.*, 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include, but are not limited to, poly-Arg-RRRRRRR (SEQ ID NO:4); PTD-5-RRQRRTSKLMKR (SEQ ID NO:5); Transportan GWTLNSAGYLLGKINL-KALAALAKKIL (SEQ ID NO:6); KALA-WEAKLAKA-LAKALAKHLAKALAKALKCEA (SEQ ID NO:7); and RQIKIWFQNRRMKWKK (SEQ ID NO:8).

In some embodiments, the fusion protein includes an endosomal escape sequence that improves delivery of the protein to the interior of the cell. Endosomal escape sequences are known in the art, see for example, Barka, et al., *Histochem. Cytochem.*, 48(11):1453-60 (2000) and Wadia and Stan, *Nat. Med.*, 10(3):310-5 (2004).

ii. Targeting Signal or Domain

In some embodiments, the Akt3 fusion protein is optionally modified to include one or targeting signals or domains. The targeting signal or sequence can be specific for a host, tissue, organ, cell, organelle, an organelle such as the nucleus, or cellular compartment. Moreover, the compositions disclosed here can be targeted to other specific intercellular regions, compartments, or cell types.

In some embodiments, the targeting signal binds to a ligand or receptor which is located on the surface of a target cell such as to bring the fusion protein and cell membranes sufficiently close to each other to allow penetration of the fusion protein into the cell. Additional embodiments are directed to specifically delivering the fusion protein to specific tissue or cell types. For example, in some embodiments, the fusion protein includes a targeting moiety that directs that fusion protein to the lympho nodes, or specifically targets immune cells, more preferably nTreg, iTreg, or conventional T cells.

In a preferred embodiment, the targeting molecule is selected from the group consisting of an antibody or antigen binding fragment thereof, an antibody domain, an antigen, a cell surface receptor, a cell surface adhesion molecule, a viral envelope protein and a peptide selected by phage display that binds specifically to a defined cell.

Targeting domains to specific cells can be accomplished by modifying the disclosed fusion proteins to include specific cell and tissue targeting signals. These sequences target specific cells and tissues, but in some embodiments the interaction of the targeting signal with the cell does not occur through a traditional receptor:ligand interaction. The eukaryotic cell includes a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the fusion protein can be altered by changing the targeting signal. In one specific embodiment, fusion proteins are provided that enable the addition of cell surface antigen specific antibodies to the fusion protein for targeting fusion protein.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

Another embodiment provides an antibody or antigen binding fragment thereof bound to the disclosed recombinant polypeptides acting as the targeting signal. The antibodies or antigen binding fragment thereof are useful for directing the fusion protein to a cell type or cell state. In one embodiment, the fusion protein possesses an antibody binding domain, for example from proteins known to bind antibodies such as Protein A and Protein G from *Staphylococcus aureus*. Therefore, in some embodiments the disclosed fusion proteins include an antibody binding domain from Protein A or Protein G. Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting domain includes all or part of an antibody that directs the fusion protein to the desired target cell type or cell state. Antibodies can be monoclonal or polyclonal, but are preferably monoclonal. Antibodies can be derived from human genes and specific for cell surface markers, and can be produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Additional embodiments are directed to specifically delivering the fusion protein to intracellular compartments or organelles. Eukaryotic cells contain membrane bound structures or organelles. Organelles can have single or multiple membranes and exist in both plant and animal cells. Depending on the function of the organelle, the organelle can consist of specific components such as proteins and cofactors. The polypeptides delivered to the organelle can enhance or contribute to the functioning of the organelle. Some organelles, such as mitochondria and chloroplasts, contain their own genome. Nucleic acids are replicated, transcribed, and translated within these organelles. Proteins are imported and metabolites are exported. Thus, there is an exchange of material across the membranes of organelles. Exemplary organelles include the nucleus, mitochondrion, etc.

b. Peptide or Polypeptide Linker Domain

The disclosed Akt3 fusion proteins optionally contain a peptide or polypeptide linker domain that separates the Akt3 polypeptide from the second polypeptide. Suitable peptide/polypeptide linker domains include naturally occurring or non-naturally occurring peptides or polypeptides. Peptide linker sequences are at least 1, 2, 3, 4, 5, or more amino acids in length. Preferably the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser, Gly-Ser-Gly-Ser (SEQ ID NO:9), Ala-Ser, Gly-Gly-Gly-Ser (SEQ ID NO:10), (Gly$_4$-Ser)$_3$ (SEQ ID NO:11) and (Gly$_4$-Ser)$_4$ (SEQ ID NO:12). Additional flexible peptide/polypeptide sequences are well known in the art.

3. Isolated Nucleic Acid Molecules

Isolated nucleic acid sequences encoding Akt3 polypeptides, fusions fragments and variants thereof are also disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-Akt3 proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The nucleic acid sequences encoding Akt3 polypeptides include genomic sequences. Also disclosed are mRNA sequence wherein the exons have been deleted. Other nucleic acid sequences encoding Akt3 polypeptides, such polypeptides that include the above-identified amino acid sequences and fragments and variants thereof, are also disclosed. Nucleic acids encoding Akt3 fusion polypeptides may be optimized for expression in the expression host of choice. Codons may be substituted with alternative codons encoding the same amino acid to account for differences in codon usage between the organism from which the Akt3 nucleic acid sequence is derived and the expression host. In this manner, the nucleic acids may be synthesized using expression host-preferred codons.

Nucleic acids can be in sense or antisense orientation, or can be complementary to a reference sequence encoding a Akt3 polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding Akt3 polypeptides can be administered to subjects in need thereof to increase Akt3 bioavailability. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

Vectors encoding Akt3 polypeptides, fusion, fragments, and variants thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the Akt3 polypeptides or fusion polypeptides described herein.

The vectors can be used to express Akt3, or variants, or fragments, or fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides can be administered directly to lymphoid tissues or tumors. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding polypeptides or fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

4. Other Compounds that Increase the Bioactivity of Akt3

In some embodiments, the compositions include a compound that increases bioactivity of endogenous Akt3. Such compounds include factors that increase the expression of or increase the half-life of endogenous Akt3. Factors that increase expression of endogenous Akt3 include, for example, Akt3 transcription factors. Akt3 transcription factors can be provided as a recombinant polypeptide, or an isolated nucleic acid encoding the transcription factor.

In some embodiments the factor that increases expression of endogenous Akt3 or increase the half-life of endogenous Akt3 is a small molecule.

B. Compositions for Decreasing the Bioactivity of Akt3

Compositions including one or more compounds for decreasing the bioactivity of Akt3 are disclosed. In some embodiments, the compound is an inhibitory Akt3 polypeptide, an inhibitory fusion protein including an Akt3 polypeptide; a small molecule or peptidomimedic antagonist of Akt3, or an inhibitory nucleic acid that targets genomic or expressed Akt3 nucleic acids (e.g., Akt3 mRNA), or a vector that encode an inhibitory nucleic acid. The preferred embodiments, the inhibitory protein, peptidomimedic, or small molecule antagonist binds to blocks the catalytic domain of Akt3, or otherwise prevents Akt3 from binding to or to its substrate(s) or Down regulation of Akt3 can decrease, or increase the reduction of, expression of IL-10 and TGFβ inhibitory cytokines in nTreg and decrease, or prevent an increase in, the overall suppressive ability of the cells. Down regulation of Akt3 in conventional T cells can decrease, or prevent an increase in, the induction level iTreg.

In some embodiments, the compound reduces the bioavailability of Akt3 and one or more other isoforms of Akt (e.g., Akt1, Akt2, or a combination thereof). Therefore, in some embodiments the compound is a "pan" Akt inhibitor. In preferred embodiments, the compound has a higher specificity, a higher affinity, or a combination thereof for Akt3 compared to Akt1, Akt2, or both Akt1 and Akt2. In the most preferred embodiments, the compound is an Akt3 specific inhibitor. Akt3 inhibition can be competitive, non-competitive, uncompetitive, product inhibition, or suicide inhibition. Exemplary inhibitors are described below. Other inhibitors are discussed in U.S. Pat. No. 6,809,194.

1. Inhibitory Akt3 Polypeptides

In some embodiments, the compound that decreases the bioavailability of Akt3 is an inhibitory Akt3 polypeptide. Inhibitory Akt3 polypeptides are typically non-functional fragments or variants of Akt3. For example, an inhibitory Akt3 polypeptide can be a fragment or variant of Akt3 that can bind to an Akt3 substrate but has reduced kinase activity compared to endogenous Akt3, or preferably, does not phosphorylate the substrate. Therefore, in some embodiments, the inhibitory peptide competes with endogenous Akt3 for binding to Akt3 substrates, thereby reducing the bioavailability of the endogenous Akt3. Preferred inhibitory peptides bind to an Akt3 substrate and prevent binding of endogenous Akt3 from binding to and/or phosphorylating the substrate. In some embodiments, the inhibitor polypeptide binds to the substrate with higher affinity or specificity than Akt3.

For example in a preferred embodiment, the inhibitory peptide has one or more substitutions, deletions, or insertions in the kinase domain, C-terminal regulatory region, or a combination thereof that reduce the ability of Akt3 to be fully activated. In some embodiments the inhibitory polypeptide is a known variant or fragment of Akt3 that lacks kinase activity, for example a variant or fragment thereof that has the sequence of SEQ ID NO:2 or 3, wherein Thr-305, Ser-472, or both Thr-305 and Ser-472 with reference to SEQ ID NO:2 is mutated or deleted. In some embodiments, the variant contains one or more substitutions, deletions, or insertions that disrupt the interaction between the PH domain and TCL1A and thereby reduce or prevent Akt3 phosphorylation and activation, but do not completely block the ability of Akt3 from binding to a substrate.

2. Small Molecules, Substrate Mimics, and Peptidomimetics a. Small Molecules

In the some embodiments the compound that reduces Akt3 bioactivity is a compound that binds to Akt3 and reduces or prevents Akt3 kinase activity or the binding specificity or affinity of Akt3 to a substrate of Akt3. In some embodiments, the compound is a small molecule. The term "small molecule" generally refers to small organic compounds having a molecular weight of more than about 100 and less than about 2,500 Daltons, preferably between 100 and 2000, more preferably between about 100 and about 1250, more preferably between about 100 and about 1000, more preferably between about 100 and about 750, more preferably between about 200 and about 500 Daltons. The small molecules can include cyclical carbon or heterocyclic structures and/or aromatic or polyaromatic structures substituted with one or more functional groups.

Small molecule inhibitors of Akt3 are known in the art and include, for example, GSC-0068, MK-2206, GSK690693, AT7867, and AZD5363. Preferred dosages and routes of administration for each of the compounds are discussed in more detail below, however, generally, the compounds can be administered to humans in an amount from about 0.0001 mg/kg of body weight to about 1,000 mg/kg of body weight per day. Generally, for intravenous injection or infusion, dosage may be lower than for other methods of delivery.

GSC-0068 has the structure:

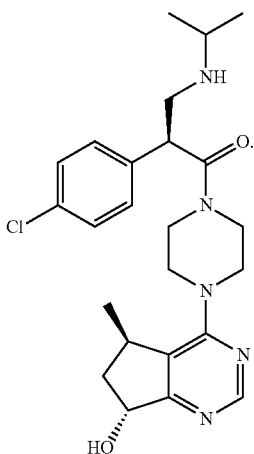 [SMILES: CC(C)NC[C@@H](C(=O)N1CCN(c2ncnc3c2[C@H](C)C[C@H]3O)CC1)c1ccc(Cl)cc1]

GDC-0068 is a highly selective pan-Akt inhibitor targeting Akt1/2/3 with IC50 of 5 nM/18 nM/8 nM, 620-fold selectivity over PKA. Discovery and preclinical pharmacology of GDC-0068 and other selective ATP-competitive Akt inhibitors for the treatment of human tumors are discussed in Blake et al., *J Med Chem.*, 27; 55(18):8110-27 (2012). Epub 2012 Sep. 18.

GDC-0068 has been administered orally at ~100 mg/kg/day for treating cancer in a mouse model. In an open label, dose escalation phase Ib clinical trial evaluating the safety and pharmacology of GDC-0068 in combination with either Taxotere (docetaxel) or mFOLFOX6 (fluoropyrimine) plus oxaliplatin in patients with advanced solid tumors, the drug was found to be safe and well tolerated up to the single agent maximum tolerated dose (600 mg) (Yan et al., *Poster B*154, *AACR-NCI-EORTC International Conference: Molecular Targets and Cancer Therapeutics*, San Francisco, Calif., Nov. 12-16, 2011). Therefore, in some embodiments, the GDC-0068 compositions disclosed herein include 0.1 mg to 1,000 mg, preferably 1 mg to 750 mg, more preferably, 25 mg to 600 mg per day. In a particular embodiment, the drug is administered 21 days on, followed by 7 days off. In some embodiments, the amount of GDC-0068 used to modulate an immune response is lower than the amount used to treat cancer.

MK-2206 has the structure:

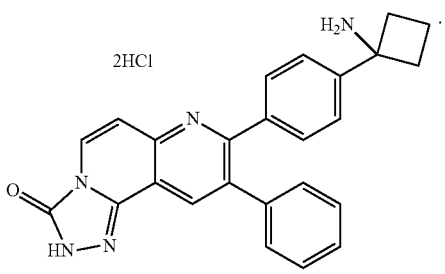 [SMILES: NC1(c2ccc(-c3nc4ccn5c(=O)[nH]nc5c4cc3-c3ccccc3)cc2)CCC1]

MK-2206 2HCl is a highly selective inhibitor of Akt1/2/3 with IC50 of 8 nM/12 nM/65 nM, respectively; no inhibitory activities against 250 other protein kinases observed.

MK-2206 2HCl has been administered at a dosage of 120 mg/kg and 240 mg/kg in a mouse model. In a first-in-man clinical trial of the oral pan-Akt inhibitor MK-2206 in patients with advanced solid tumors.

Thirty-three patients received MK-2206 at 30, 60, 75, or 90 mg on alternate days. Dose-limiting toxicities included skin rash and stomatitis, establishing the MTD at 60 mg. Therefore, in some embodiments, the MK-2206 2HCl compositions disclosed herein include 0.1 mg to 1,000 mg, preferably 1 mg to 500 mg, more preferably, 5 mg to 60 mg per day.

GSK690693 is a pan-Akt inhibitor targeting Akt1/2/3 with 1050 of 2 nM/13 nM/9 nM. GSK690693 has the structure:

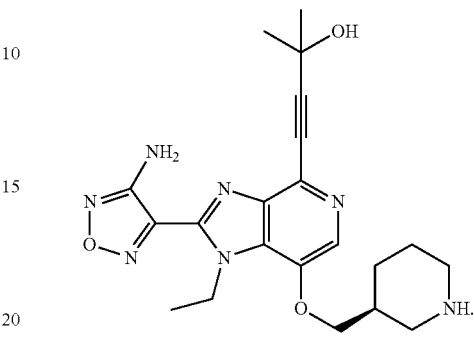

GSK690693 has been administered at a dosage of 30 mg/kg/day in a mouse model (Rhodes, et al., *Cancer Res.*, 68(7):2366-74 (2008). A dosage range of 0.1-4.8 mg/mL by slow infusion over 1-4 hours, once or twice weekly, has been proposed for the treatment of cancer.

AT7867 is a potent ATP-competitive inhibitor of Akt1/2/3 and p70S6K/PKA with 1050 of 32 nM/17 nM/47 nM and 85 nM/20 nM, respectively. AT7867 has the structure:

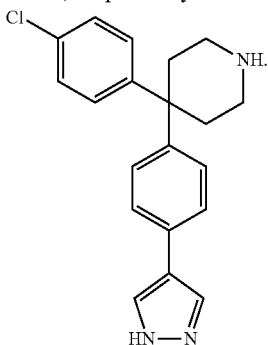

AT7867 has been administered at dosages of 20 mg/kg i.p. and 90 mg/kg p.o. every three days in a mouse model (Grimshaw, et al., *Mol Cancer Ther*, 9(5), 1100-1110 (2010)).

AZD5363 potently inhibits all isoforms of Akt(Akt1/Akt2/Akt3) with IC50 of 3 nM/8 nM/8 nM. AZD5363 has the structure:

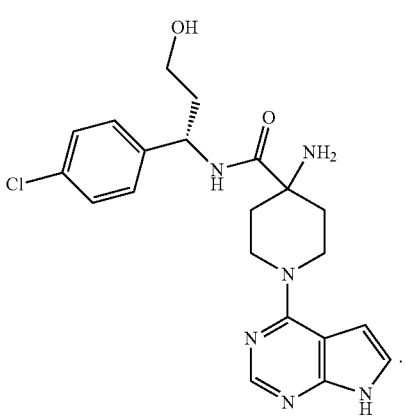 [SMILES: NC1(C(=O)N[C@@H](CCO)c2ccc(Cl)cc2)CCN(c2ncnc3[nH]ccc23)CC1]

AZD5363 has been administered orally at dosages of 100 mg/kg, 130 mg/kg, 200 mg/kg, and 300 mg/kg in a mouse model. In a clinical trial testing the effect of AZD5363 on patients with advanced solid tumors, an intermittent dosing schedule of 480 mg twice a day was generally well tolerated AACR Press Releases "Akt Inhibitor AZD5363 Well Tolerated, Yielded Partial Response in Patients With Advanced Solid Tumors", Apr. 7, 2013. Therefore, in some embodiments, AZD5363 compositions disclosed herein include 1 mg to 1,000 mg, preferably 100 mg to 750 mg, more preferably, 400 mg to 600 mg twice per day.

b. Molecular Sinks and Peptidomimetics

In some embodiments, the compound that inhibits Akt3 bioactivity is a peptide substrate mimic or peptidomimetic that binds to the active site of Akt3 and reduces the bioavailability Akt3 for its endogenous substrates. Peptide substrate mimic or peptidomimetic can be a fragment of an endogenous substrate of ATK3 that includes the amino acid residue of the endogenous Akt3 substrate that is phosphorylated by ATK3. In some embodiments, the peptide substrate mimic or peptidomimetic can bind to the active site of Akt3 and be phosphorylated by Akt3. In some embodiments, the peptide or peptidomimetic can bind to the active site of Akt3, but cannot be phosphorylated by ATK3. For example, in some embodiments, the peptide or peptiodmimetic is a fragment of a substrate of Akt3 that includes the residue that is phosphorylated by Akt3, but wherein the residue is mutate to residue that cannot be phosphorylated. In this way, peptide substrate mimics and peptidomimedics serve as a molecular sink for Akt3 and reduce its bioavailability for its endogenous substrates. A broad range of substrates for Akts have been identified, including, but not limited to, transcription factors (e.g. FOXO1), kinases (GSK-3, Raf-1, ASK, Chk1) and other proteins with important signaling roles (e.g. Bad, MDM2).

2. Inhibitory Nucleic Acids for Antagonizing Akt3

Inhibitory nucleic acids can be used to antagonize Akt3 by inhibiting or down regulating expression of Akt3 mRNA. Thus, in some embodiments, the Akt3 antagonist is an inhibitory nucleic acid that silences gene expression. Any inhibitory nucleic acids based the mRNA sequence of SEQ ID NO:1, or gene sequence encoding SEQ ID NO:1, or a nucleic acid sequence encoding the polypeptide of SEQ ID NO:2 or 3, or a fragment or variant thereof.

Inhibitory nucleic acid technologies are known in the art and include, but are not limited to, antisense oligonucleotides, catalytic nucleic acids such as ribozymes and deoxyribozymes, aptamers, triplex forming nucleic acids, external guide sequences, and RNA interference molecules (RNAi), particularly small nucleic acid molecules, such as short interfering nucleic acid (siNA), short interfering RNA (siRNA), double-stranded RNA (dsRNA), micro-RNA (mRNA), and short hairpin RNA (shRNA) molecules capable of mediating RNA interference (RNAi).

a. RNA Interference

Gene silencing by RNAi was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

In some embodiments the inhibitory nucleic acid is an siRNA. SiRNA is typically a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. Sequence specific gene or isoform specific silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded. Therefore, the double-stranded structure may be formed by a single self-complementary RNA strand or two separate complementary RNA strands. RNA duplex formation may be initiated either inside or outside the plant cell.

Suitable inhibitory nucleic acids can contain one or more modified bases, or have a modified backbone to increase stability or for other reasons. For example, the phosphodiester linkages of natural RNA may be modified to include at least one of a nitrogen or sulfur heteroatom. Moreover, nucleic acids comprising unusual bases, such as inosine, or modified bases, such as tritylated bases, to name just two examples, can be used. It will be appreciated that a great variety of modifications have been made to nucleic acids that serve many useful purposes. The term nucleic acids as it is employed herein embraces such chemically, enzymatically or metabolically modified forms of nucleic acids, provided that it is derived from an endogenous template.

The sequence of at least one strand of the RNAi molecule contains a region complementary to at least a part of the target mRNA sufficient for the RNAi molecule to specifically hybridize to the target mRNA. In one embodiment, one strand of the RNAi molecule is substantially identical to at least a portion of the target mRNA.

In one embodiment, the inhibitory nucleic acid has 100% sequence identity with at least a part of the target mRNA. However, inhibitory nucleic acids having 70%, 80% or greater than 90% or 95% sequence identity may be used.

Thus sequence variations that might be expected due to genetic mutation, strain polymorphism, or evolutionary divergence can be tolerated.

RNAi molecules includes small RNA molecules which are single stranded or double stranded RNA molecules generally less than 200 nucleotides in length. Such molecules are generally less than 100 nucleotides and usually vary from 10 to 100 nucleotides in length. The duplex region of a double stranded RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). While the optimum length of the double stranded RNA may vary according to the target sequence and experimental conditions, the duplex region of the RNA may be at least 19, 20, 21, 22, 23, 25, 50, 100, 200, 300, 400 or more nucleotides long. In a preferred format, small RNA molecules, such as siRNA and shRNA have 11, 12, 13, 14, 15, 16, 17, 18, 19, 20, 21, 22, 23, 24, 25, 26, 27, 28, 29 or 30 nucleotides. Preferably, the nucleotides are contiguous, consecutive nucleotides of complementary to a target mRNA sequence, for example Atk3 mRNA.

In vivo, the RNAi molecule may be synthesized using recombinant techniques well known in the art (see e.g., Sambrook, et al., Molecular Cloning; A Laboratory Manual, Third Edition (2001)). For example, bacterial cells can be transformed with an expression vector which comprises the DNA template from which double stranded RNA is to be derived. Alternatively, the cells in which inhibition of gene or isoform expression is desired may be transformed with an expression vector or by other means. Bidirectional transcription of one or more copies of the template may be by endogenous RNA polymerase of the transformed cell or by a cloned RNA polymerase (e.g., T3, T7, SP6) coded for by the expression vector or a different expression vector Inhibition of gene or isoform expression may be targeted by specific transcription in an organ, tissue, or cell type; an environmental condition (e.g. temperature, chemical); and/or engineering transcription at a developmental stage or age, especially when the RNAi molecule is synthesized in vivo. RNAi molecules may also be delivered to specific tissues or cell types using known gene delivery systems. The production of siRNA from a vector is commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. are any shRNA designed as described above based on the sequences for the herein disclosed inflammatory mediators.

b. Aptamers

In some embodiments, a compound that reduces the bioavailability of Akt3 is an aptamer. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules as well as large molecules, such as reverse transcriptase. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules are known in the art.

c. Ribozymes

In some embodiments, a compound that reduces the bioavailability of Akt3 is a ribozyme. Ribozymes are nucleic acid molecules that are capable of catalyzing a chemical reaction, either intramolecularly or intermolecularly. Ribozymes are thus catalytic nucleic acids. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Examples of how to make and use ribozymes to catalyze a variety of different reactions are known in the art.

d. Triplex Forming Nucleic Acids

In some embodiments a compound that reduces the bioavailability of Akt3 are triplex forming nucleic acids. Triplex forming nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Examples of how to make and use triplex forming molecules to bind a variety of different target molecules are known in the art.

e. External Guide Sequences

In some embodiments a compound that reduces the bioavailability of Akt3 are external guide sequences (EGSs). EGSs are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Examples of how to make and use EGS molecules to facilitate cleavage of a variety of different target molecules are known in the art.

C. Formulations

Formulations of and pharmaceutical compositions including one or more of the disclosed compounds are provided. Dosage ranges for specific small molecules are discussed above based on pre-clinical and clinical trial data. Generally, dosage levels, for the compounds disclosed herein are between about 0.0001 mg/kg of body weight to about 1,000 mg/kg, more preferably of 0.001 to 500 mg/kg, more preferably 0.01 to 50 mg/kg of body weight daily are administered to mammals. In some embodiments, polypeptides or nucleic acids are administered in a dosage of 0.01 to 50 mg/kg of body weight daily, preferably about 0.1 to 20 mg/kg. In some embodiments, nucleic acid dosages can range from about 0.001 mg to about 1,000 mg, more preferable about 0.01 mg to about 100 mg per administration (e.g., daily; or once, twice, or three times weekly, etc.)

1. Delivery Vehicles

The active agents can be administered and taken up into the cells of a subject with or without the aid of a delivery vehicle. Appropriate delivery vehicles for the disclosed active agents are known in the art and can be selected to suit the particular active agent. For example, in some embodiments, the active agent(s) is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

The active agent(s) can be incorporated into a delivery vehicle prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. The release point and/or period of release can be varied as discussed above.

2. Pharmaceutical Compositions

Pharmaceutical compositions including the disclosed compounds, with or without a delivery vehicle, are provided. Pharmaceutical compositions can be for administration by parenteral (intramuscular, intraperitoneal, intravenous (IV) or subcutaneous injection), enteral, transmucosal (nasal, vaginal, rectal, or sublingual), or transdermal (either passively or using iontophoresis or electroporation) routes of administration or using bioerodible inserts and can be formulated in dosage forms appropriate for each route of administration.

In certain embodiments, the compositions are administered locally, for example by injection directly into a site to be treated (e.g., into a tumor). In some embodiments, the compositions are injected or otherwise administered directly into the vasculature onto vascular tissue at or adjacent to the intended site of treatment (e.g., adjacent to a tumor). Typically, local administration causes an increased localized concentration of the compositions which is greater than that which can be achieved by systemic administration.

a. Formulations for Parenteral Administration

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids. The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

c. Formulations for Pulmonary and Mucosal Administration

Active agent(s) and compositions thereof can be applied formulated for pulmonary or mucosal administration. The administration can include delivery of the composition to the lungs, nasal, oral (sublingual, buccal), vaginal, or rectal mucosa.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per cm³, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

d. Transdermal

Transdermal formulations may also be prepared. These will typically be ointments, lotions, sprays, or patches, all of which can be prepared using standard technology. Transdermal formulations can include penetration enhancers.

III. Method of Modulating Akt3

The disclosed compositions for modulating Akt3 can be used to modulate immune response by increasing or decreasing a suppressive function of nTreg, increasing or decreasing induction of iTreg, or a combination thereof. In some embodiments, the compositions are administered systemically. In some embodiments, the compositions are administered locally or regionally. For example, in some embodiments, compositions are delivered to or specifically target the tissue or organs in need of modulation. In some embodiments, Treg are modulated by targeting or delivering the compositions to the lymph nodes. In some embodiments, nTreg are modulated by targeting or specifically delivering the compositions to the thymus or spleen. In some embodiment, iTreg are modulated by targeting or specifically delivering the compositions conventional T cells outside the thymus.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Exemplary symptoms, pharmacologic, and physiologic effects are discussed in more detail below.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based measuring the symptom, pharmacologic, or physiologic indicator in one or more subjects that do not have the disease or condition to be treated (e.g., healthy subjects). In some embodiments, the effect of the treatment is compared to a conventional treatment that is known the art. For example, if the disease to be treated is cancer, and conventional treatment could a chemotherapeutic agent.

In some embodiments, the immune modulating compositions disclosed herein are administered in combination with one or more additional active agents. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such formulations typically include an effective amount of one or more of the disclosed immune modulating compounds. The different active agents can have the same, or different mechanisms of action. In some embodiments, the combination results in an additive effect on the treatment of the disease or disorder. In some embodiments, the combinations results in a more than additive effect on the treatment of the disease or disorder.

The Examples below also show that Smad2 and Smad3 were significantly decreased in the nucleus and cytosolic Smad2 was dramatically increased in iTregs from Akt3 KO mice. In contrast, nuclear translocation of both Smad molecules was increased and cytosolic Smad2 was decreased in absence of Akt1. The absence of Akt2 did not affect the levels of nuclear and cytosolic Smads. Taken together these data indicate that the possible isoform that interacts with Smads and responsible for their "neutralization" and thus FoxP3 decrease is Akt1. Thus, when Akt1 is absent there is no inhibition for Smads nuclear translocation and there is more protein detected in nucleus and more FoxP3 iTregs induced. The Akt3 isoform could block the Akt1-mediated inhibition of Smad nuclear translocation, since in the absence of Akt3 both total Akt1 and its phosphorylation are increased. Therefore, in Akt3 KO iTregs Smad nuclear translocation is decreased and less iTregs are induced (FIG. 18).

Therefore, in some embodiments, the disclosed compounds or methods of use specifically increase or decrease bioavailability of Akt3 without increasing or decreasing the bioavailability of Akt1, Akt2, or the combination thereof. In other embodiments, the compounds modulate Akt3 and Akt1, Akt2, or a combination there. In a particular embodiment, a composition is utilized that increases the bioavailability of Akt3 and decrease the bioavailability of Akt1. Alternatively, in another particular embodiment, a composition is utilized that decreases the bioavailability of Akt3 and increases the bioavailability of Akt1.

A. Reducing Immune Stimulatory Responses and Increasing Immune Suppressive Responses 1. Methods of Treatment In some embodiments compositions that increase the bioactivity of Akt3 are administered to a subject in an effective amount to reduce an immune stimulatory response, increase an immune suppressive response, or a combination thereof. The Examples below illustrated that Akt3 regulates the function and induction of natural and induced Treg. Therefore Akt3 expression levels can be modulated to alter the function and induction of Treg. In some embodiments, a composition that increases the bioactivity of Akt3 is administered to a subject in an effective amount to increase a suppressive function of nTreg, to increase the induction of conventional Treg into iTreg, or a combination thereof. In some embodiments, an increase the suppressive function of nTreg is measured as an overall decrease in secretion or presence of anti-inflammatory cytokines or chemokines, for example, TGFβ and IL10. Alternatively, decreased suppressive function can be measured as an overall increase in pro-inflammatory molecules such as IL-1β, TNF-α, IFN-γ, IL-17, IL-6, IL-23, IL-22, IL-21, and MMPs. Induction of conventional Treg into iTreg can be measured as differentiation of CD4+CD25− cells into Foxp3+ cells. In some embodiments, this is measured as a reduction in the number of CD4+ conventional T cells, or an increase in the number of Foxp3+ T cells.

2. Diseases to Treat

The compositions that increase the bioactivity of Akt3 disclosed herein can be used to inhibit immune-mediated tissue destruction for example in a setting of inflammatory responses, autoimmune and allergic diseases, and transplant rejection.

a. Inflammatory and Autoimmune Disorders

In certain embodiments, the disclosed compositions are used to treat an inflammatory response or autoimmune disorder in a subject. For example, the disclosed methods can be used to prophylactically or therapeutically inhibit, reduce, alleviate, or permanently reverse one or more symptoms of an inflammatory response or autoimmune disorder. An inflammatory response or autoimmune disorder can be inhibited or reduced in a subject by administering to the subject an effective amount of a composition in vivo, or cells modulated by the composition ex vivo.

Representative inflammatory responses and autoimmune diseases that can be inhibited or treated include, but are not limited to, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

b. Transplant Rejection

In another embodiment, the disclosed compositions and methods for inducing or perpetuating a suppressive immune response can be used prophylactically or therapeutically to reduce or inhibit graft rejection or graft verse host disease. Transplant rejection occurs when a transplanted organ or tissue is not accepted by the body of the transplant recipient. Typically rejection occurs because the immune system of the recipient attacks the transplanted organ or tissue. The disclosed methods can be used to promote immune tolerance of the transplant or graft by the receipt by administering to the subject an effective amount of a composition in vivo, or cells modulated by the composition ex vivo.

i. Transplants

The transplanted material can be cells, tissues, organs, limbs, digits or a portion of the body, for example the human body. The transplants are typically allogenic or xenogenic. The disclosed compositions are administered to a subject in an effective amount to reduce or inhibit transplant rejection. The compositions can be administered systemically or locally by any acceptable route of administration. In some embodiments, the compositions are administered to a site of transplantation prior to, at the time of, or following transplantation. In one embodiment, compositions are administered to a site of transplantation parenterally, such as by subcutaneous injection.

In other embodiments, the compositions are administered directly to cells, tissue or organ to be transplanted ex vivo. In one embodiment, the transplant material is contacted with the compositions prior to transplantation, after transplantation, or both.

In other embodiments, the compositions are administered to immune tissues or organs, such as lymph nodes or the spleen.

The transplant material can also be treated with enzymes or other materials that remove cell surface proteins, carbohydrates, or lipids that are known or suspected of being involved with immune responses such as transplant rejection.

(a). Cells

Populations of any types of cells can be transplanted into a subject. The cells can be homogenous or heterogenous. Heterogeneous means the cell population contains more than one type of cell. Exemplary cells include progenitor cells such as stem cells and pluripotent cells which can be harvested from a donor and transplanted into a subject. The cells are optionally treated prior to transplantation as mention above.

(b). Tissues

Any tissue can be used as a transplant. Exemplary tissues include skin, adipose tissue, cardiovascular tissue such as veins, arteries, capillaries, valves; neural tissue, bone marrow, pulmonary tissue, ocular tissue such as corneas and lens, cartilage, bone, and mucosal tissue. The tissue can be modified as discussed above.

(c). Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of the composition to inhibit or reduce chronic transplant rejection relative to a control.

ii. Graft-Versus-Host Disease (GVHD)

The disclosed compositions and methods can be used to treat graft-versus-host disease (GVHD) by administering an effective amount of the composition to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

In another embodiment, the disclosed compositions and methods for inducing or perpetuating a suppressive immune response can be used prophylactically or therapeutically to suppress allergies and/or asthma and/or inflammation in lungs. Allergies and/or asthma and/or inflammation in the lungs can be suppressed, inhibited or reduced in a subject by administering to the subject an effective amount of a composition that increases Akt3 bioavailability in vivo, or cells modulated by a composition that increases Akt3 bioavailability ex vivo as described above.

In some embodiments, the composition induces IDO-competent cells to have increased IDO enzyme activity in the lungs. In one embodiment, the IDO-competent cells are lung epithelial cells.

It has been reported that the induction of pulmonary IDO by immunostimulatory polynucleotides protects the lung from Th2-driven lung inflammation and experimental asthma. Likewise, the induction of IDO in a SCID/Th1 transfer model attenuated Th1-driven lung inflammation. However, in this case, in contrast to the Th2 transfer model, the inhibition of lung inflammation by immunostimulatory polynucleotide administration was buffered by the intrinsic ability of Th1 cells to induce pulmonary IDO activity after OVA challenge, most probably via the production of IFNγ, (Hayashi, et al., *J. Clin. Investig.,* 114(2):270-279 (2004)). Therefore, the compositions can be delivered in an effective amount to induce a level of IDO activity that can inhibit Th-mediated lung inflammation, for example by (a) depleting tip availability in the microenvironment; (b) promoting the generation of various toxic tip metabolites, which induce Th cell death; (c) inducing generation of other compounds, e.g., formylkynurenine, through a reaction that removes oxygen radicals at inflammatory sites; and/or (d) in the case of Th2-mediated lung inflammation, inhibiting the generation of 5-hydroxytryptamine, a potent airway constrictor.

3. Methods of Modulating Vaccines

Tolerogenic vaccines deliver antigens with the purpose of suppressing immune responses and promoting robust long-term antigen-specific immune tolerance. For example, Incomplete Freund's Adjuvant (IFA) mixed with antigenic peptides stimulates Treg proliferation (and/or accumulation) and IFA/Insulin peptide prevents type I diabetes onset in susceptible mice, though this approach is ineffective in reversing early onset type I diabetes (Fousteri, G., et al., 53:1958-1970 (2010)). The compositions and methods disclosed herein are also useful for controlling the immune response to an antigen. For example, a composition that increases the bioavailability of Akt3 can be used to potentiate the effect of a tolerizing vaccine. In some embodiments, the tolerizing vaccine is a DNA vaccine. DNA immunization provides a non-replicating transcription unit that serves as a template for the synthesis of proteins or protein segments to induce antigen specific immune responses in the host (Ho, et al., *Autoimmunity,* 39(8):675-682 (2006)). Injection of DNA encoding foreign antigens promotes immunity against a variety of microbes and tumors. In autoimmune diseases DNA vaccines induce tolerance to the DNA-encoded self-antigens. The DNA-encoded self-antigen depends on the disease to be treated, and can be determined by one of skill in the art.

Compositions that increase the bioavailability of Akt3 can be used to enhance the immune suppressive effect of DNA vaccines designed to induce tolerance to the DNA-encoded self-antigens. The compositions can be administered in combination with or as a component of, a tolerizing vaccine composition. A vaccine typically contains an antigen, or a nucleic acid encoding an antigen as in DNA vaccines, and optionally may include one or more adjuvants. The antigen, for example, a DNA-encoded self-antigen, depends on the disease to be treated, and can be determined by one of skill in the art. A composition that increases the bioavailability of Akt3 administered in combination with a vaccine is typically administered in amount effective to increase immunosuppression compared to administration of the vaccine alone.

Suitable adjuvants can be, but are not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

4. Methods of Modulating Mucosal Tolerance

Mucosal tolerance, also referred to as oral tolerance, is the absence of an immune response to an antigen that is exposed through mucosal surfaces such as the gastrointestinal tract, genitourinary, or bronchial tissue. Mucosal tolerance is a natural immunologic process driven by the presence of an exogenous antigen, whereby external agents (antigens) that gain access to the body via a natural route become part of the self (Iian, *Human Immunol.,* 70:768-776 (2009)). Antigen-specific therapy via mucosal tolerance is a physiologic means to manipulate immune responses, is nontoxic, and can be administered on a chronic basis. When self-antigens are administered, mucosal tolerance can be used to treat inflammatory responses and autoimmune diseases.

Compounds that increase the bioavailability of Akt3 can be used to enhance mucosal tolerance, particular as it applies to treatment of autoimmune diseases and inflammatory responses. The compositions can be administered in combination with, or as a component of, a mucosal tolerance composition. A mucosal tolerance composition typically contains an antigen, for example a whole protein, a peptide, an altered peptide or a nucleic acid encoding an antigen, and optionally may include one or more adjuvants. Suitable adjuvants are known in the art and discussed above with respect to tolerizing vaccines. The antigen, for example a self-antigen, depends on the disease to be treated, and can be determined by one of skill in the art.

A compound that can increase the bioavailability of Akt3 can be administered in combination with a mucosal tolerance composition is typically administered in amount effective to increase immunosuppression compared to administration of the mucosal tolerance composition alone. The mucosal composition is typically administered to a mucosa, for example, oral, nasal, and gastrointestinal mucosa. Routes of administration of the antigen include, but are not limited to oral, nasal, and parenteral. A composition that increase the bioavailability of Akt3 can be administered in combination with a mucosal tolerance composition can be administered via the same route, or a separate route of administration, such as those described above. Mucosal tolerance may be particularly effective for treatment of the autoimmune diseases discussed above, for example, encephalomylelitis, myasthenia gravis, Neuritis, uveoretinitis, insulin dependent diabetes mellitus (type I diabetes), and arthritis (Xiao, et al., *Clin. Immunol. Immunopath.*, 85(2):119-28 (1997)).

5. Combination Therapies

The disclosed compositions for increasing the bioactivity of Akt3 can be administered alone or in combination with one, two, three, or more additional active agents. In some embodiments, the additional active agent is one that is known in the art for treatment of inflammation, inflammatory responses, autoimmune diseases and disorders, etc.

Additional therapeutic agents include, but are not limited to, immunosuppressive agents (e.g., antibodies against other lymphocyte surface markers (e.g., CD40, alpha-4 integrin) or against cytokines), other fusion proteins (e.g., CTLA-4-Ig (ORENCIA®), TNFR-Ig (ENBREL®)), TNF-α blockers such as ENBREL, REMICADE, CIMZIA and HUMIRA, cyclophosphamide (CTX) (i.e. ENDOXAN®, CYTOXAN®, NEOSAR®, PROCYTOX®, REVIMMUNE™), methotrexate (MTX) (i.e. RHEUMATREX®, TREXALL®), belimumab (i.e. BENLYSTA®), or other immunosuppressive drugs (e.g., cyclosporin A, FK506-like compounds, rapamycin compounds, or steroids), anti-proliferatives, cytotoxic agents, or other compounds that may assist in immunosuppression.

In some embodiments, the additional therapeutic agent functions to inhibit or reduce T cell activation and cytokine production through a separate pathway. In one such embodiment, the additional therapeutic agent is a CTLA-4 fusion protein, such as CTLA-4 Ig (abatacept). CTLA-4 Ig fusion proteins compete with the co-stimulatory receptor, CD28, on T cells for binding to CD80/CD86 (B7-1/B7-2) on antigen presenting cells, and thus function to inhibit T cell activation. In some embodiments, the additional therapeutic agent is a CTLA-4-Ig fusion protein known as belatacept. Belatacept contains two amino acid substuitutions (L104E and A29Y) that markedly increase its avidity to CD86 in vivo. In another embodiment, the additional therapeutic agent is Maxy-4.

In another embodiment, the second therapeutic is a second agent that induces IDO expression. Second therapeutics that induce IDO expression are described in Johnson, et al., *Immunotherapy*, 1(4):645-661 (2009), and U.S. Pat. Nos. 6,395,876 and 6,451,840. In one embodiment, the second therapeutic that induces IDO expression is a nanoparticle loaded with an expression vector that encodes an IDO1 or IDO2 polypeptide.

In another embodiment, the second therapeutic agent preferentially treats chronic transplant rejection or GvHD, whereby the treatment regimen effectively targets both acute and chronic transplant rejection or GvHD. In another embodiment the second therapeutic is a TNF-α blocker.

In another embodiment, the second therapeutic agent increases the amount of adenosine in the serum, see, for example, WO 08/147482. In some embodiments, the second therapeutic is CD73-Ig, recombinant CD73, or another agent (e.g. a cytokine or monoclonal antibody or small molecule) that increases the expression of CD73, see for example WO 04/084933. In another embodiment the second therapeutic agent is Interferon-beta.

In some embodiments, the compositions are used in combination or succession with compounds that increase Treg activity or production. Exemplary Treg enhancing agents include but are not limited to glucocorticoid fluticasone, salmeteroal, antibodies to IL-12, IFNγ, and IL-4; vitamin D3, and dexamethasone, and combinations thereof. Antibodies to other proinflammatory molecules can also be used in combination or alternation with the disclosed compositions. For example, antibodies can bind to IL-6, IL-23, IL-22 or IL-21.

In some embodiments, the second or more active agent is a rapamycin compound. As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art.

In some embodiments, the second or more active agent is an FK506-like compound. The phrase "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds are known in the art. Preferably, the language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, flucloronone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

B. Decreasing Immune Suppressive Responses and Increasing Immune Stimulatory Responses 1. Methods of Treatment In some embodiments compositions that decrease the bioactivity of Akt3 are administered to a subject in an effective amount to increase an immune stimulatory response, decrease an immune suppressive response, or a combination thereof. The Examples below illustrated that Akt3 regulates the function and induction of natural and induced Treg. Therefore Akt3 expression levels can be modulated to alter the function and induction of Treg. In some embodiments, a composition that decreases the bioactivity of Akt3 is administered to a subject in an effective amount to decrease a suppressive function of nTreg, to decrease the induction of conventional Treg into iTreg, or a combination thereof. In some embodiments, a decrease in the suppressive function of nTreg is measured as an overall decrease in secretion or presence of pro-inflammatory cytokines or chemokines, for example, TGFβ and IL10. Other pro-inflammatory molecules that can be decreased include, but are not limited to, IL-1β, TNF-α, IFN-γ, IL-17, IL-6, IL-23, IL-22, IL-21, and MMPs. Induction of conventional Treg into iTreg can be measured as differentiation of CD4+ CD25− cells into Foxp3+ cells. In some embodiments, this is measured as an increase in the number of CD4+ conventional T cells, or a decrease in the number of Foxp3+ T cells.

2. Diseases to Treat

Compositions that reduce the bioavailability can be used to increase an immune stimulatory response in subject. In some embodiments, the subjects have cancer, an infectious disease, or another condition in which the immune response is desired. In some embodiments, the subject does not have cancer or does not have an infectious disease. In some embodiments, the subject has an infectious disease, but does not have cancer. In some embodiments, the subject has cancer, but does not have an infectious disease.

a. Cancer

The compounds for decreasing the bioavailability of Akt3 provided herein are generally useful in vivo and ex vivo as immune response-stimulating therapeutics. In general, the disclosed compounds for decreasing the bioavailability of Akt3 are useful for treating a subject having or being predisposed to any disease or disorder to which the subject's immune system mounts an immune response. The ability of compounds for decreasing the bioavailability of Akt3 to inhibit or reduce Treg mediated immune suppression enables a more robust immune response to be possible. The disclosed compositions are useful to stimulate or enhance immune stimulating or activating responses involving T cells.

The disclosed compounds for decreasing the bioavailability of Akt3 are useful for stimulating or enhancing an immune response in host for treating cancer. The compound can be administered to a subject to a subject in an amount effective to stimulate T cells in the subject. The types of cancer that can be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic.

Malignant tumors that can be treated can be classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

b. Infections

The compounds for decreasing the bioavailability of Akt3 are generally useful in vivo and ex vivo as immune response-stimulating therapeutics. In a preferred embodiment, the compositions are useful for treating infections in which T cell exhaustion or T cell anergy has occurred causing the infection to remain with the host over a prolonged period of time. Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus. It will be appreciated that other infections can also be treated using the compounds for decreasing the bioavailability of Akt3. The disclosed compositions are also useful as part of a vaccine. In a preferred embodiment, the type of disease to be treated or prevented is a chronic infectious disease caused by a bacterium, virus, protozoan, helminth, or other microbial pathogen that enters intracellularly and is attacked, i.e., by cytotoxic T lymphocytes.

Chronic infections in human and animal models are associated with a failure of the host immune response to generate and sustain functional $CD8^+$ and $CD4^+$ T-cell populations, which also results in poor antibody responses to neutralize infectivity. This loss of function is referred to as T cell exhaustion. T cell anergy is a tolerance mechanism in which the lymphocyte is intrinsically functionally inactivated following an antigen encounter, but remains alive for an extended period of time in a hyporesponsive state. One method for treating chronic infection is to revitalize exhausted T cells or to reverse T cell exhaustion in a subject as well as overcoming T cell anergy. Therefore, in some embodiments, a compound for decreasing the bioavailability of Akt3 is administered to a subject in an effective amount to reverse T cell exhaustion, overcoming T cell anergy, or a combination thereof in a subject in need thereof.

Because viral infections are cleared primarily by T-cells, an increase in T-cell activity is therapeutically useful in situations where more rapid or thorough clearance of an infective viral agent would be beneficial to an animal or human subject. Thus, the compounds can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the compounds can be administered topically to treat viral skin diseases such as herpes lesions or shingles, or genital warts. Pharmaceutical formulations containing a compound for decreasing the bioavailability of Akt3 can also be administered to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Histoplasma, Hyphomicrobium, Legionella, Leishmania, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni*.

3. Use of Compounds for Decreasing the Bioavailability of Akt3 in Vaccines a. Vaccine-Related Methods The compounds for decreasing the bioavailability of Akt3 can be administered alone or in combination with any other suitable treatment. In one embodiment the compound can be administered in conjunction with, or as a component of a vaccine composition. The disclosed compounds can be administered prior to, concurrently with, or after the administration of a vaccine. In one embodiment the compound is administered at the same time as administration of a vaccine.

Compounds for decreasing the bioavailability of Akt3 can be administered in conjunction with prophylactic vaccines, which confer resistance in a subject to subsequent exposure to infectious agents, or in conjunction with therapeutic vaccines, which can be used to initiate or enhance a subject's immune response to a pre-existing antigen, such as a viral antigen in a subject infected with a virus.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

The compounds induce an improved effector cell response such as a CD4 T-cell immune response, against at least one of the component antigen(s) or antigenic compositions compared to the effector cell response obtained with the corresponding composition without the compound. The term "improved effector cell response" refers to a higher effector cell response such as a CD4 T cell response obtained in a human patient after administration of the vaccine composition than that obtained after administration of the same composition without a compound for decreasing the bioavailability of Akt3. Such a formulation can advantageously be used to induce anti-antigen effector cell response capable of detection of antigen epitopes presented by MHC class II molecules.

The improved effector cell response can be obtained in an immunologically unprimed patient, i.e. a patient who is seronegative to the antigen. This seronegativity may be the result of the patient having never faced the antigen (so-called "naïve" patient) or, alternatively, having failed to respond to the antigen once encountered. Preferably the improved effector cell response is obtained in an immunocompromised subject such as an elderly, typically 65 years of age or above, or an adult younger than 65 years of age with a high risk medical condition ("high risk" adult), or a child under the age of two.

The improved effector cell response can be assessed by measuring the number of cells producing any of the following cytokines: (1) cells producing at least two different cytokines (CD40L, IL-2, IFNγ, TNF-α, IL-17); (2) cells producing at least CD40L and another cytokine (IL-2, TNF-α, IFNγ, IL-17); (3) cells producing at least IL-2 and another cytokine (CD40L, TNF-alpha, IFNγ, IL-17); (4) cells producing at least IFNγ and another cytokine (IL-2, TNF-α, CD40L, IL-17); (5) cells producing at least TNF-α and another cytokine (IL-2, CD40L, IFNγ, IL-17); and (6) cells producing at least IL-17 and another cytokine (TNF-alpha, IL-2, CD40L, IFNγ, IL-17)

An improved effector cell response is present when cells producing any of the above cytokines will be in a higher amount following administration of the vaccine composition compared to the administration of the composition without a compound for decreasing the bioavailability of Akt3. Typically at least one, preferably two of the five conditions mentioned above will be fulfilled. In a preferred embodiment, cells producing all five cytokines (CD40L, IL-2, IFNγ, TNF-α, IL-17) will be present at a higher number in the vaccinated group compared to the un-vaccinated group.

The immunogenic compositions may be administered by any suitable delivery route, such as intradermal, mucosal e.g. intranasal, oral, intramuscular or subcutaneous. Other delivery routes are well known in the art. The intramuscular delivery route is preferred for the immunogenic compositions. Intradermal delivery is another suitable route. Any suitable device may be used for intradermal delivery, for example short needle devices. Intradermal vaccines may also be administered by devices which limit the effective penetration length of a needle into the skin. Jet injection devices which deliver liquid vaccines to the dermis via a liquid jet injector or via a needle which pierces the stratum corneum and produces a jet which reaches the dermis can also be used. Jet injection devices are known in the art. Ballistic powder/particle delivery devices which use compressed gas to accelerate vaccine in powder form through the outer layers of the skin to the dermis can also be used.

Additionally, conventional syringes can be used in the classical Mantoux method of intradermal administration.

Another suitable administration route is the subcutaneous route. Any suitable device may be used for subcutaneous delivery, for example classical needle. Preferably, a needle-free jet injector service is used. Needle-free injectors are known in the art. More preferably the device is pre-filled with the liquid vaccine formulation.

Alternatively the vaccine is administered intranasally. Typically, the vaccine is administered locally to the nasopharyngeal area, preferably without being inhaled into the lungs. It is desirable to use an intranasal delivery device which delivers the vaccine formulation to the nasopharyngeal area, without or substantially without it entering the lungs. Preferred devices for intranasal administration of the vaccines are spray devices. Nasal spray devices are commercially available. Nebulizers produce a very fine spray which can be easily inhaled into the lungs and therefore does not efficiently reach the nasal mucosa. Nebulizers are therefore not preferred. Preferred spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are commercially available.

Preferred intranasal devices produce droplets (measured using water as the liquid) in the range 1 to 200 μm, preferably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is another feature of an intranasal delivery system for use with the vaccines. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines.

The immunogenic composition may be given in two or more doses, over a time period of a few days, weeks or months. In one embodiment, different routes of administration are utilized, for example, for the first administration may be given intramuscularly, and the boosting composition can be administered through a different route, for example intradermal, subcutaneous or intranasal.

The improved effector cell response conferred by the immunogenic composition may be ideally obtained after one single administration. The single dose approach is extremely relevant in a rapidly evolving outbreak situation including bioterrorist attacks and epidemics. In certain circumstances, especially for the elderly population, or in the case of young children (below 9 years of age) who are vaccinated for the first time against a particular antigen, it may be beneficial to administer two doses of the same composition. The second dose of the same composition (still considered as 'composition for first vaccination') can be administered during the on-going primary immune response and is adequately spaced in time from the first dose. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals.

In a specific embodiment, the administration of the immunogenic composition alternatively or additionally induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in vitro differentiation (see Example sections, e.g. methods of Elispot B cells memory).

In a still another embodiment, the immunogenic composition increases the primary immune response as well as the CD8 T cell response. The administration of a single dose of the immunogenic composition for first vaccination provides better sero-protection and induces an improved CD4 T– cell, or CD8 T-cell immune response against a specific antigen compared to that obtained with the un-adjuvanted formulation. This may result in reducing the overall morbidity and mortality rate and preventing emergency admissions to hospital for pneumonia and other influenza-like illness. This method allows inducing a CD4 T cell response which is more persistent in time, e.g. still present one year after the first vaccination, compared to the response induced with the un-adjuvanted formulation.

Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

b. Immunogenic and Vaccine Compositions

The dose of a compound for decreasing the bioavailability of Akt3 enhances an immune response to an antigen in a human. As discussed above, compounds for decreasing the bioavailability of Akt3 described herein can be administered as a component of a vaccine to promote, augment, or enhance the primary immune response and effector cell activity and numbers. When used as part of a vaccine, the compound can be administered in separate, or in the same admixture with an immunogenic composition or as part of an immunogenic protocol. Vaccines include antigens, and optionally other adjuvants and targeting molecules.

i. Antigens

Antigens can be peptides, proteins, polysaccharides, saccharides, lipids, nucleic acids, or combinations thereof. The antigen can be derived from a virus, bacterium, parasite, protozoan, fungus, histoplasma, tissue or transformed cell and can be a whole cell or immunogenic component thereof, e.g., cell wall components or molecular components thereof.

Suitable antigens are known in the art and are available from commercial, government and scientific sources. In one embodiment, the antigens are whole inactivated or attenuated organisms. These organisms may be infectious organisms, such as viruses, parasites and bacteria. The antigens may be tumor cells or cells infected with a virus or intracellular pathogen such as gonorrhea or malaria. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

(a) Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain, or a combination of strains, such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

(b) Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.*

(c) Parasitic Antigens

Antigens of parasites can be obtained from parasites such as, but not limited to, antigens derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

(d) Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAAO205, Mum-2, Mum-1, 2, and 3, neo-PAP, myosin class I, OS-9, pm1-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Tumor antigens, such as BCG, may also be used as an immunostimulant to adjuvant.

ii. Adjuvants

Optionally, the vaccines may include an adjuvant. The adjuvant can be, but is not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor. Other co-stimulatory molecules, including other polypeptides of the B7 family, may also be administered. Such proteinaceous adjuvants may be provided as the full-length polypeptide or an active fragment thereof, or in the form of DNA, such as plasmid DNA.

4. Combination Therapies

The disclosed compositions for increasing the bioactivity of Akt3 can be administered alone or in combination with one, two, three, or more additional active agents. In some embodiments, the additional active agent is one that is known in the art for treatment of cancer, infections, or administered in combination with a vaccine, etc. The additional therapeutic agents are selected based on the condition, disorder or disease to be treated. For example, compositions for increasing the bioactivity of Akt3 can be co-administered with one or more additional agents that function to enhance or promote an immune response.

For example, the disclosed compositions can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, doxorubicin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

In a preferred embodiment, the additional therapeutic agent is cyclophosphamide. Cyclophosphamide (CPA, Cytoxan, or Neosar) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANAO) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Ref. Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(-)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

Additional therapeutic agents include is an agent that reduces activity and/or number of regulatory T lymphocytes (T-regs), preferably Sunitinib (SUTENT®), or anti-TGFβ. Other additional therapeutic agents include mitosis inhibitors, such as paclitaxol, aromatase inhibitors (e.g. Letrozole), angiogenesis inhibitors (VEGF inhibitors e.g. Avastin, VEGF-Trap), TLR4 antagonists, and IL-18 antagonists.

IV. Screens for Small Molecules that Effect Bioactivity of Akt3

Modulators of the function, expression, or bioactivity of Akt3 can be identified using well known techniques and reagents. In some embodiments, the modulator increases or decreases the physical interaction between Akt3 and one or more of its substrates. Some modulators increase or decrease the function, expression, or bioavailability of Akt3.

In some embodiments, screening assays can include random screening of large libraries of test compounds. Alternatively, the assays may be used to focus on particular classes of compounds suspected of modulating the function or expression of Akt3 in cells, tissues, organs, or systems.

Assays can include determinations of protein expression, protein activity, or binding activity of Akt3. Other assays can include determinations of nucleic acid transcription or translation, for example mRNA levels, mRNA stability, mRNA degradation, transcription rates, and translation rates of Akt3.

In one embodiment, the identification of a Akt3 modulator is based on the function of ATK3 in the presence and absence of a test compound. The test compound or modulator can be any substance that alters or is believed to alter the function of Akt3. In some embodiments the test compound or modulator increases or decreases the ability of Akt3 to bind to and/or phosphorylate one or more substrates. In some embodiments the test compound or modulator increases or decreases Akt3-dependent Treg function or polarization. For example, in some embodiments the test compound or modulator increases or decreases nTreg suppressive function (e.g., secretion of IL10 or TGFβ), or increases or decreases induction of conventional T cells into iTreg, or a combination thereof compared to a control.

One exemplary method includes contacting Akt3 with at least a first test compound, and assaying for an interaction between ATK3 and the first test compound with an assay.

Specific assay endpoints or interactions that may be measured in the disclosed embodiments include binding to Akt3 substrates. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as *C. elegans* and transgenic animals.

Other screening methods include labeling Akt3 to identify a test compound. Akt3 can be labeled using standard labeling procedures that are well known and used in the art. Such labels include, but are not limited to, radioactive, fluorescent, biological and enzymatic tags.

Another embodiment provides a method for identifying a modulator of expression Akt3 by determining the effect a test compound has on the expression of Akt3 in cells. For example isolated cells or whole organisms expressing Akt3 can be contacted with a test compound. Expression Akt3 can be determined by detecting Akt3 protein expression or Akt3 mRNA transcription or translation. Suitable cells for this assay include, but are not limited to, immortalized cell lines, primary cell culture, or cells engineered to express Akt3. Compounds that increase or decrease the expression or bioavailability of Akt3 can be selected.

One example of a cell free assay is a binding assay. While not directly addressing function, the ability of a modulator to bind to a target molecule, for example binding Akt3 to a substrate, is strong evidence of a related biological effect. The binding of a molecule to a target may, in and of itself, be inhibitory, due to steric, allosteric or charge-charge interactions or may downregulate or inactivate Akt3. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

Techniques for high throughput screening of compounds are known in the art. Large numbers of small peptide test compounds can be synthesized on a solid substrate, such as plastic pins or some other surface. Round polypeptide is detected by various methods.

V. Kits

Medical kits are also disclosed. The medical kits can include, for example, a dosage supply of one or more of the compound disclosed herein. The active agent(s) can be supplied alone (e.g., lyophilized), or in a pharmaceutical composition. The active agent(s) can be in a unit dosage, or in a stock that should be diluted prior to administration. In some embodiments, the kit includes a supply of pharmaceutically acceptable carrier. The kit can also include devices for administration of the active agent(s) or composition(s), for example, syringes. The kits can include printed instructions for administering the compound in a use as described above.

EXAMPLES

Example 1: Akt3 is Upregulated in nTregs Compared to Tconv Cells

Results

Figure 1B:
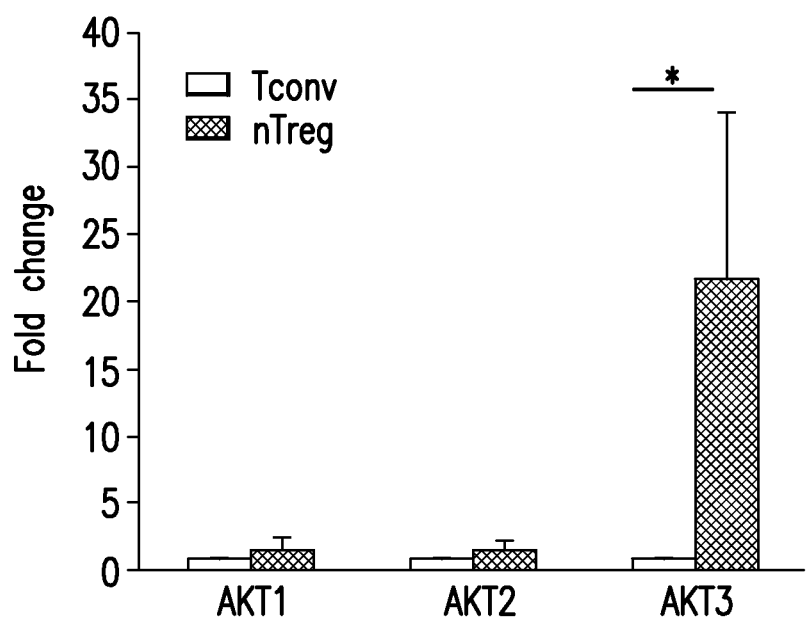
FIG. 1B is a bar graph showing the fold change in Akt1, Akt2, and Akt3 mRNA expression as determined by real time PCR analysis of RNA from CD4+CD25− convention T cells (Tconv) and CD4+CD25+ regulatory T cells (Treg) enriched from total splenocytes and stimulated with anti-CD3, anti-CD28 and IL-2 for 72 hours (Fold change was calculated by the ΔΔCT method after normalizing to BACTIN and expression of different Akt isoforms are normalized to 1 in CD4+CD25− culture and compared the expression levels in CD4+CD25+ culture; n=3, *P<0.05.).

The PI3K-Akt pathway is important for the signaling of the TCR, CD28, and IL-2 in T cells (Carson, et al., *Annals of the New York Academy of Sciences*, 1103, 167-178 (2007); Crellin, et al., *Blood*, 109, 2014-2022 (2007a); Crellin, et al., *Journal of Immunological Methods*, 324, 92-104 (2007b); Walsh, et al., *J. Clin. Invest.*, 116, 2521-2531. (2006)). Tconv and Treg exhibit different pattern of TCR signaling responses, therefore, the expression of Akt isoforms between Tconv and nTreg cells was examined. Akt1 and Akt2 protein expression was found to be similar in both cell types however Akt3 protein expression was over five-fold higher in nTregs than in Tconv (FIG. 1A). Analysis of mRNA levels revealed that Akt3 mRNA was also dramatically upregulated in nTregs compared to Tconv cells (FIG. 1B).

Next, the activity of Akt isoforms in Tconv and Treg cells in response to TCR, CD28, and IL-2 stimulation was tested. At baseline levels, Tconv cells express higher levels of phosphorylated Akt isoforms compared to Tregs. However, upon stimulation all three isoforms were almost equally phosphorylated in Tconv cells whereas Akt3 was phosphorylated to a greater extent than either Akt1 or Akt2 in nTregs and the level of phosphorylated Akt3 in nTregs was five-fold that of Tconv. In contrast, Akt1 and Akt2 were phosphorylated to the same extent in both Tconv and Tregs cells.

Figure 2A:
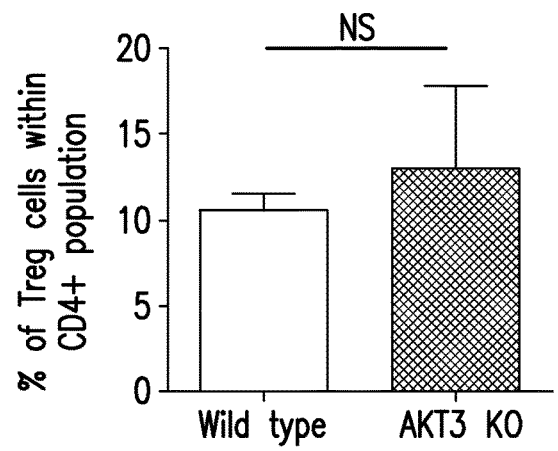
FIGS. 2A-2C are bar graphs showing the % Foxp3+CD4+ Treg with the CD4+ population (2A), % of CD4+ T cells of total T cells (2B); and % of CD8+ T cell of total T cells (2C) in wildtype and Akt3 knockout mice.
Figure 2B:
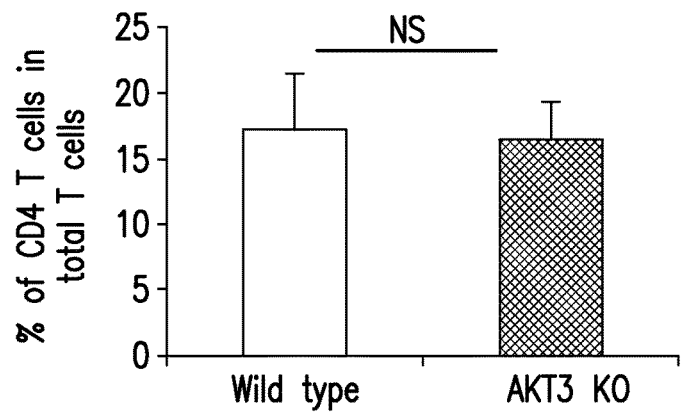
Figure 2C:
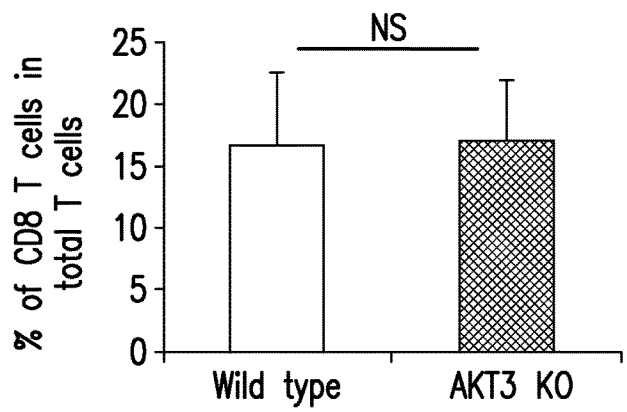
Figure 4A:
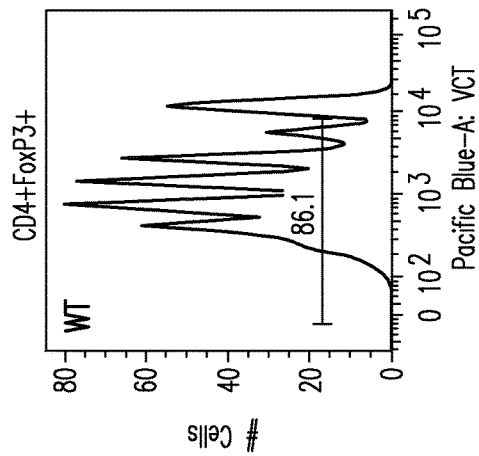
FIGS. 4A-4F are single parameter histograms showing analysis of the proliferation of CD8+ T cells (4A, 4D), CD4+FoxP3− T cells (4B, 4E), and CD4+FoxP3+ T cells (4C, 4F) by flow cytometry after activating the purified and CFSE labeled wildtype (4A-4C) and Akt3 knockout (4D-4E) cells for three days.
Figure 4B:
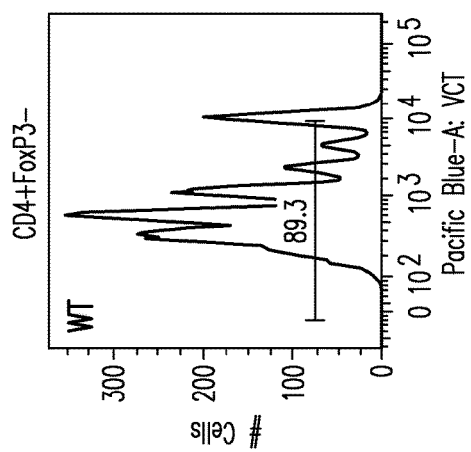
Figure 4C:
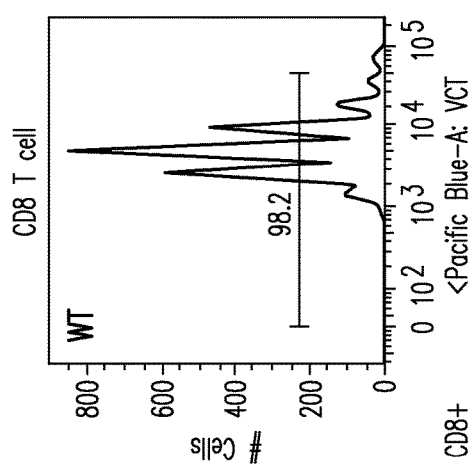
Figure 4D:
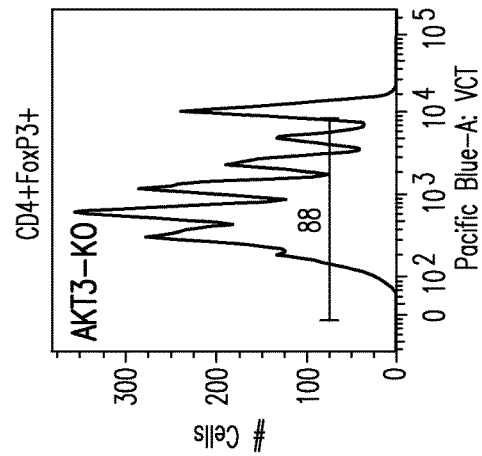
Figure 4E:
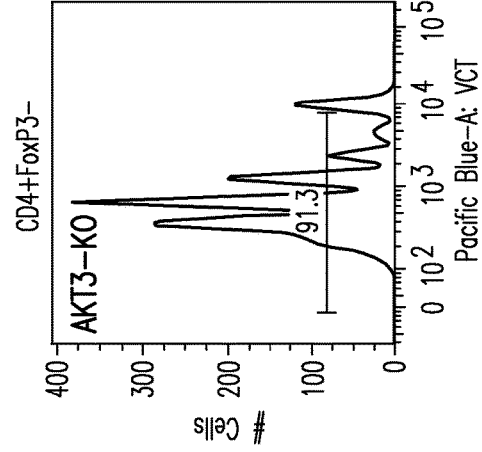
Figure 4F:
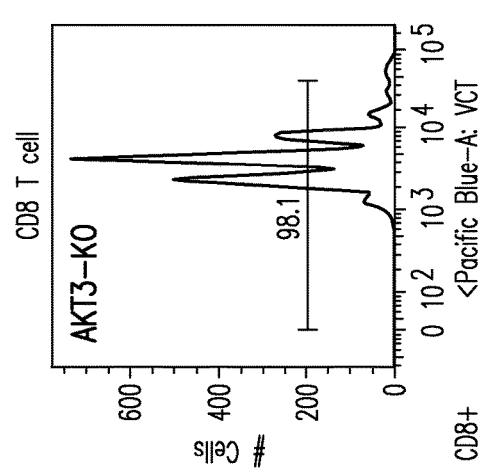

Example 2: Loss of Akt3 does not Alter Surface Marker Expression or Proliferation of nTregs Results To test whether the higher levels of total and phosphorylated Akt3 in nTreg have biological relevance, the T cells composition in Akt3 KO mice was examined. Analysis revealed that levels of splenic Tregs, CD4 and CD8 T cells in Akt3 KO mice were similar to those in wild type (WT) mice (FIG. 2A-2C).

Next the levels of surface markers that could be involved in function of nTregs on cells from Akt3 KO and WT mice were examined. The expression of Treg-specific surface markers such as GITR, CTLA-4, PD-1 and CD25 from both WT and Akt3 KO mice were similar (FIG. 3A-3D).

No differences in proliferative capacity of Tregs, CD4 and CD8 T cells from Akt3 KO compared to WT T cell subsets (FIG. 4A-4F) were observed.

Example 3: Loss of Akt3 Impairs the Suppressive Function of nTregs

Results

Figure 5:
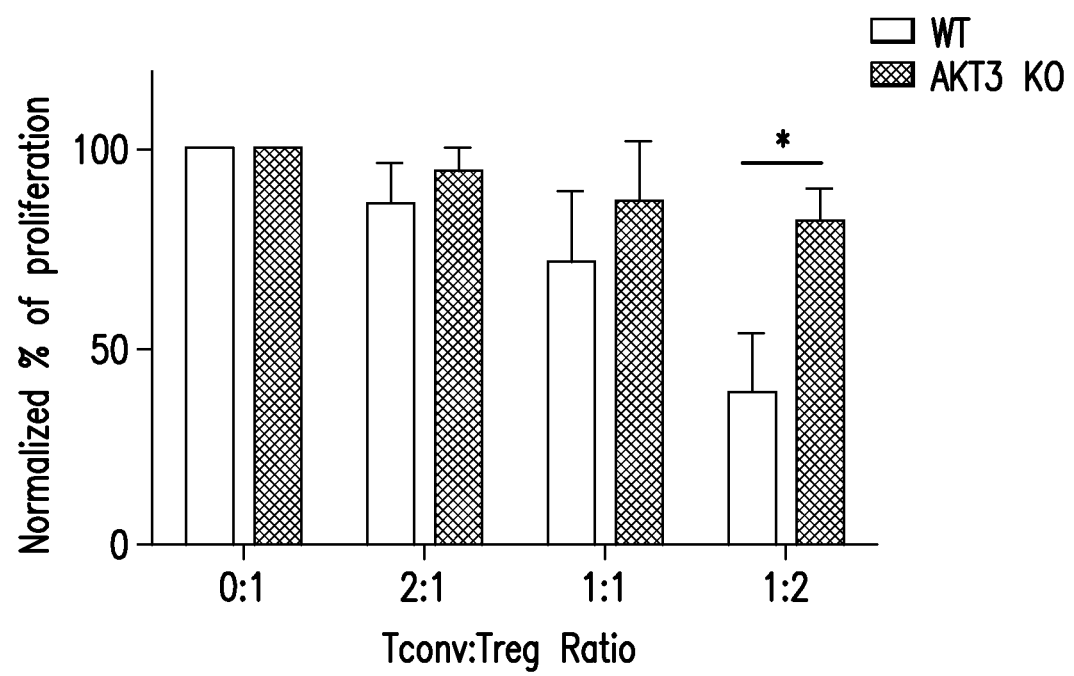
FIG. 5 is a bar graph showing the normalized % of proliferation of naive CD4+ T cells (effector T cells (Teff)) activated by antibody to CD3 (anti-CD3), anti CD28 and IL2 in the presence of various ratios of Treg cells sorted from 6-week-old wild-type or Akt3 knockout mice, measured as dilution of the cytosolic dye CFSE. n=3, *P<0.05. Data are representative of three experiments with three mice per genotype.

Next, to further test the role of Akt3 in nTreg function, the ability of nTregs purified from tumor-free Akt3 KO and WT animals to suppress the proliferation of stimulated Tconv cells in vitro was tested. CFSE-labeled Tconv cells were co-incubated with nTregs from either Akt3 KO or WT mice at different ratios and proliferation was assessed using flow cytometry CFSE dilution assay. The results show that nTregs from Akt3 KO mice had significantly impaired ($P<0.05$) suppressive function compared to nTregs from WT mice (FIG. 5).

Figure 6:
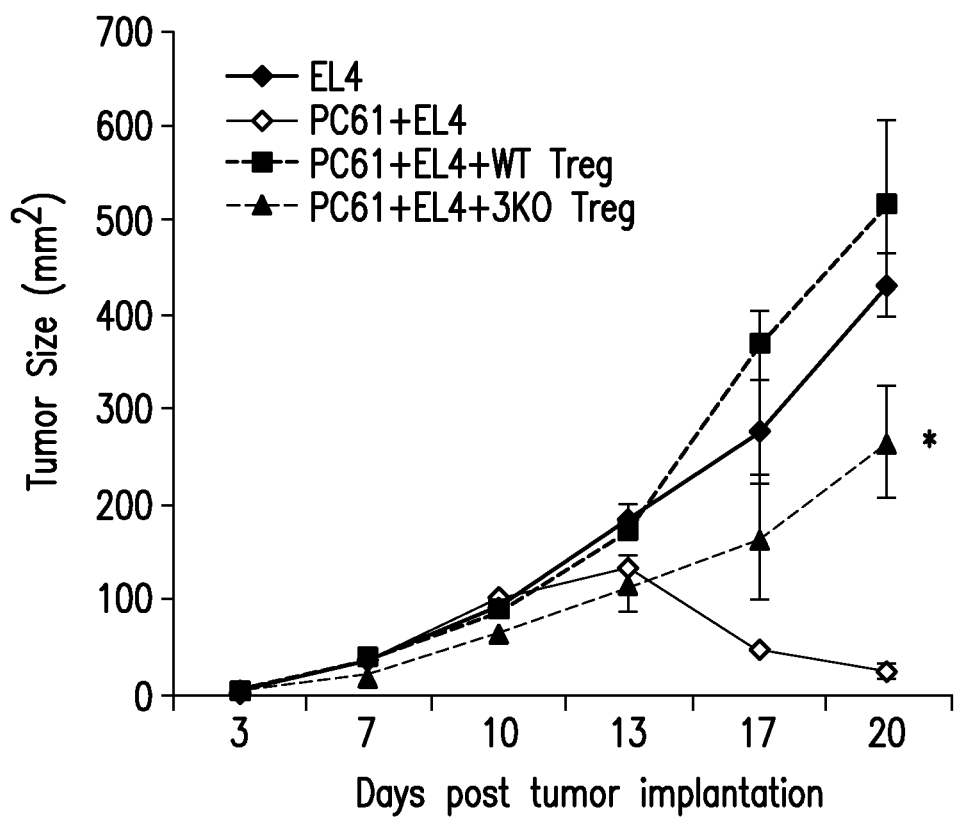
FIG. 6 is a line graph showing the EL4 tumor growth over time (days post tumor implantation) in mice treated with PC61 (administered four days before tumor inoculation) and re-infused with ex vivo stimulated Tregs from either wild-type or Akt3 knockout mice injected via tail vein four days after tumor implantation. * p<0.02.
Figure 7A:
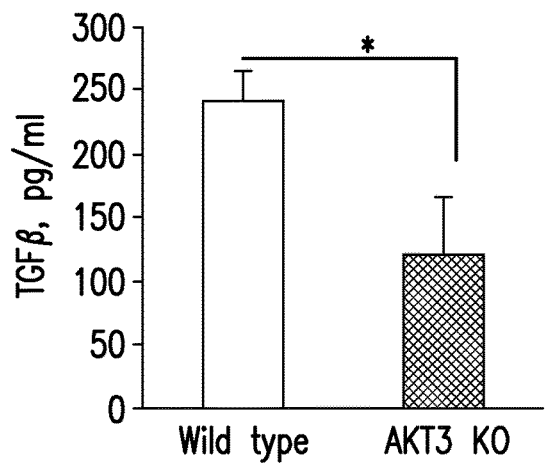
FIGS. 7A-7C are bar graphs showing the level of TGFβ (measured by ELISA) in supernatants Tconv (CD25−) and Treg (CD25+) CD4+ cells from WT (7A-7C), Akt1 (7B), Akt2 (7C), or Akt3 (7A) knockout mice enriched from total splenocytes and stimulated with anti-CD3, anti-CD28, and IL-2 for 72 h. The end point read at absorbance at 450 nm, with the correction wavelength set at 570 nm. (P<0.05, n=3).
Figure 7B:
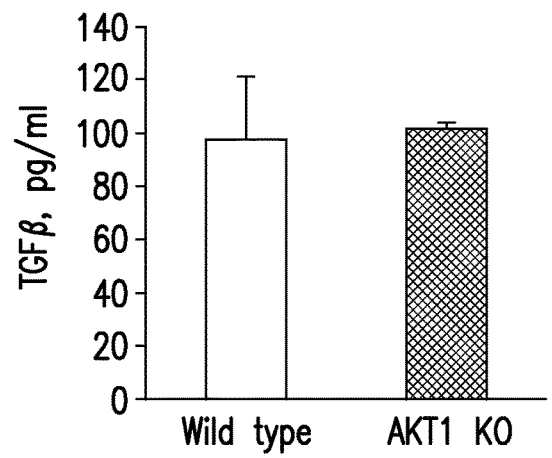
Figure 7C:
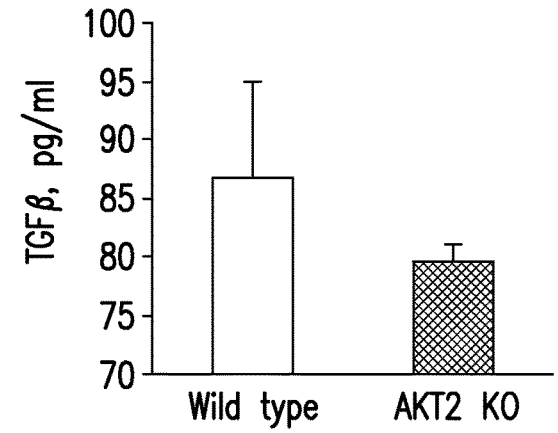

Next, the suppressive ability of nTregs from Akt3 KO and WT was tested using in vivo adoptive transfer. The EL4 tumor model was utilized. nTregs from Akt3 KO or WT mice were transplanted into tumor-bearing mice depleted of their Tregs and tumor growth was analyzed as a readout for the suppressive function of nTregs. The results show that depletion of Tregs inhibited tumor growth and re-infusion of nTregs from WT mice completely reversed that effect, indicating that EL4 tumor growth is Treg-dependent. However, re-infusion of nTregs from Akt3 KO mice only partially reversed the Treg depletion effect, resulting in significant inhibition of tumor growth when compared to either untreated mice or animals reconstituted with nTregs from WT mice (P<0.05) (FIG. 6). These data confirm that nTregs from Akt3 KO mice are significantly less suppressive compared to their WT counterparts not only in vitro but also in vivo.

Example 4: Loss of Akt3 Reduces Secretion of Anti-Inflammatory Cytokines from nTregs Results As discussed above, no differences in CD25, GITR, CTLA-4 or PD-1 expression were observed between nTregs from Akt3 KO and WT mice. To investigate another possible cause of the functional impairment of Akt3 KO, the expression levels of inhibitory cytokines (i.e. TGFβ and IL-10) secreted by nTregs were examined. The results show a significant decrease in expression of both cytokines in nTregs from Akt3 KO mice compared to WT (FIGS. 7A-7C and 8A-8B).

To understand if TGFβ and IL-10 decrease is an isoform-specific phenomenon, expression of these cytokines was also examined in nTregs from Akt1 KO and Akt2 KO mice. In contrast to Akt3, the absence of Akt1 or Akt2 does not affect the TGFβ and IL-10 levels in nTregs (FIG. 7A-7C and FIG. 8A-8B).

It was previously demonstrated that Akt regulates translation of TGFβ through phosphorylation of translation initiation factor eukaryotic initiation factor 4E (eIF4E) (Yi, et al., *J Immunol.*, 181(5):3575-85 (2008)). Therefore, to confirm that Akt3 is the isoform that controls the TGFβ translation, the phosphorylation level of eIF4E was examined in nTregs from WT and Akt-isoform knockout mice. The results show that while the level of total eIF4E protein was unchanged in nTregs from all strains of mice, the phosphorylation of eIF4E was decreased only in nTregs from Akt3 KO mice compared to WT.

Example 5: Loss of Akt3 Reduces Signaling that Modulates IL-10 Expression in nTregs Results Because IL-10 expression by nTregs was significantly decreased in Akt3 KO mice compared to WT animals, the expression levels of signaling molecules that regulate IL-10 expression were also examined. Inactivation of GSK3 through its phosphorylation by Akt has been shown to increase the levels of IL-10 (Wang, et al., *Cytokine*, 53(2):130-40 (2011) Epub 2010 Nov. 23) through the inhibition of phosphorylation of CREB (Wen, et al., *J Immunol.*, 185(11):6413-9 (2010)). Therefore, the phosphorylation of these two proteins in nTregs from Akt KO and WT mice was investigated. In contrast to nTregs from Akt1 KO and Akt2 KO mice, nTregs from Akt3 KO mice have significantly higher activation (lower phosphorylation) of GSK3b and inhibited phosphorylation of CREB compared to nTregs from WT animals. This result explains the lower expression of IL-10 in nTregs from Akt3KO mice compared to WT.

Figure 9:
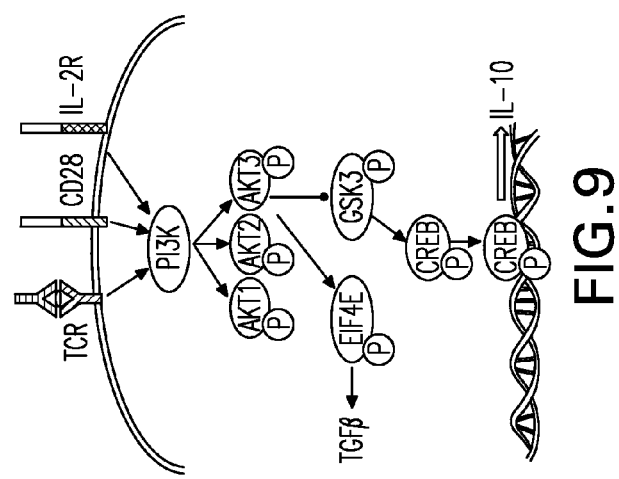
FIG. 9 is a diagram showing proposed mechanism of regulation of Treg function by different Akt isoforms.

Taken together, these results are consistent with the conclusion that Akt3 is the isoform that is solely responsible for decrease of TGFβ and IL-10 in nTregs, and thus, accountable for the impairment of suppressive function of these cells (FIG. 9). Experimental autoimmune encephalomyelitis (EAE) Akt3 KO mice were more severely affected than WT mice, further supporting the conclusion that the Akt3 isoform is important for Treg suppressive function (Tsiperson, et al., *J Immunol.*, 190(4):1528-39 (2013) Epub 2013 Jan. 18.).

Example 6: Loss of Akt3 Increases Treg-Mediate Inhibition of Tumor Growth

Results

Figure 10B:
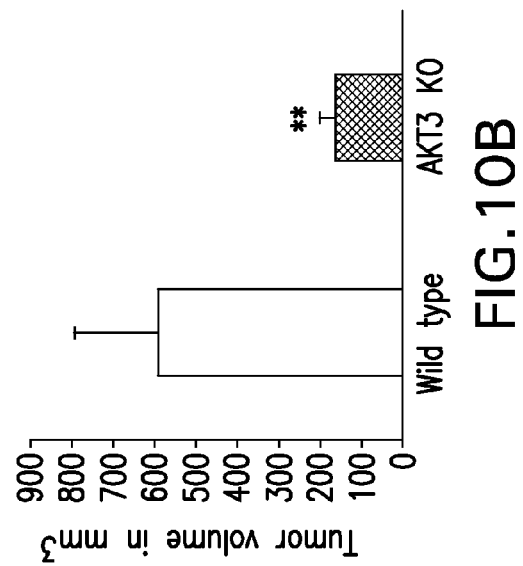
FIGS. 10A and 10B are bar graphs showing tumor volume (in mm$^3$) assessed by maximal two-dimension measurement in wildtype and Akt3 mice injected (i.p.) with TC1 (10A, (n=5)) or B16 (10B, (n=4) tumor cells and scarified after 18 to 20 days. Results are expressed as mean±SD (*p<0.05).
Figure 10A:
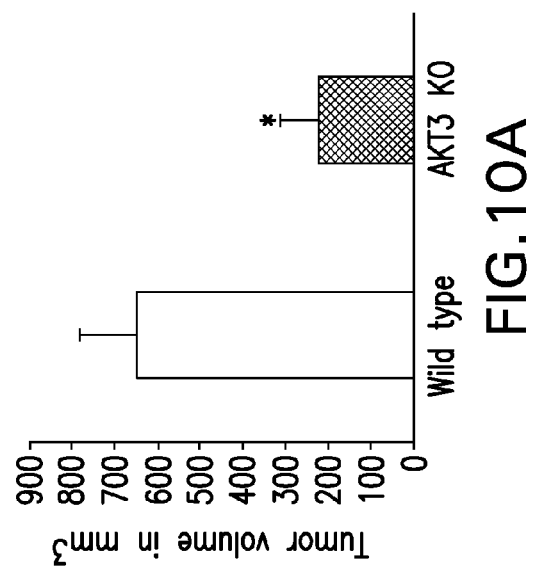

After demonstrating that suppressive function of Tregs is inhibited in absence of Akt3 and considering an important impact of Treg-mediated suppression on anti-tumor immunity, the effect of Akt3 on Treg-mediated inhibition of tumor growth was investigated. Akt3 KO mice and their WT littermates were inoculated with B16 or TC-1 tumor cells and tumor growth was monitored. Tumor growth was significantly inhibited in Akt3 KO mice compared to WT in both tumor models (FIG. 10A-10B).

Figure 11A:
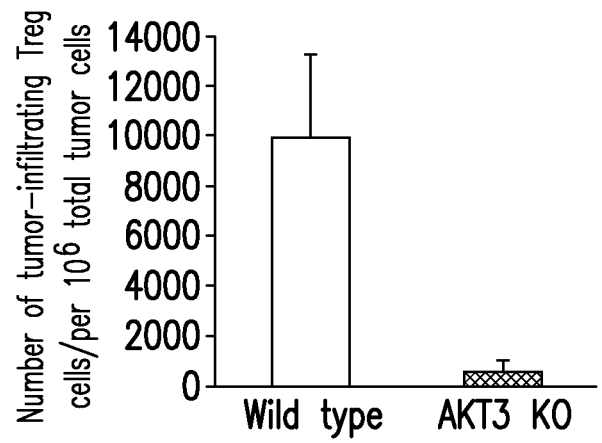
FIGS. 11A and 11B are bar graphs showing the number of tumor infiltrating Treg per $10^6$ tumor cells analyzed flow cytometrically by gating Foxp3+CD4+ T cells in CD45+ CD3+ cells isolated from wildtype and Akt3 mice injected (i.p.) with TC1 (11A, n=5) or B16 (11B, n=4) tumor cells and scarified after 18 to 20 days. Results are expressed as mean±SD (*p<0.05) (n=5).
Figure 11B:
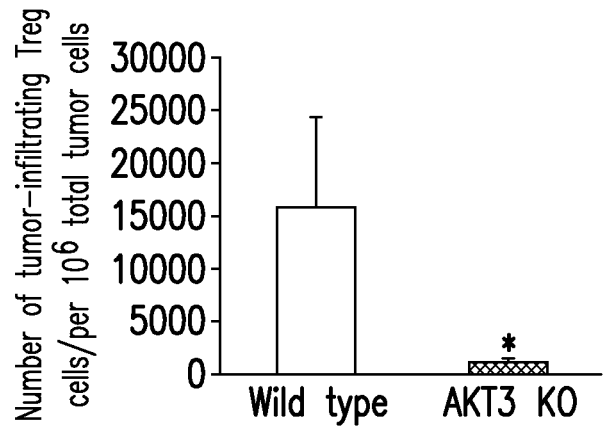

Next, the infiltration of Treg cells into the tumor was examined. Infiltration of Tregs was significantly lower in tumors of Akt3 KO mice compare to that of WT for both tumor models (FIG. 11A-11B).

Example 7: Akt3 is Upregulated in iTregs Compared to Tconv Cells

Results

Figure 12A:
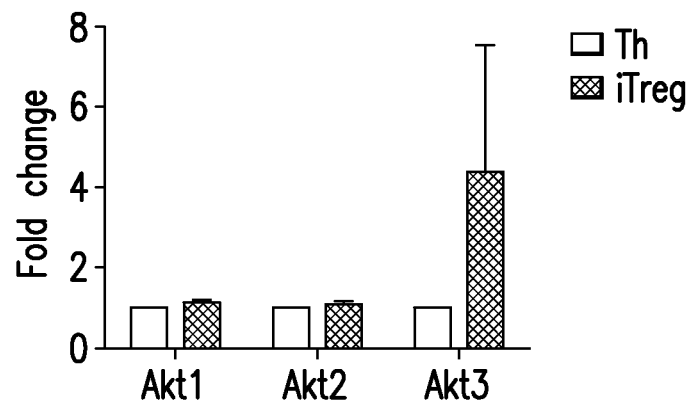
FIG. 12A is a bar graph showing the fold change in Akt1, Akt2, and Akt3 protein levels as determined by densitometry following western blots analysis of lysates of CD4+CD25− naïve T cells enriched from total splenocytes and stimulated in vitro with plate bound anti-CD3, soluble anti-CD28, and IL-2 in the presence (iTreg condition) or absence (Th condition) of TGFβ for 72 h (normalized to β-actin protein levels, n=3, *p<0.05).

Since tumor-infiltrating Tregs are composed of not only nTregs but also of de novo induced iTregs, the role of Akt3 in this subset of Tregs was also investigated. The expression of Akt isoforms and their phosphorylation were investigated using an in vitro system wherein the activation of CD4+ CD25− cells in the presence of TGFβ and IL-2 induces de novo expression of Foxp3 (Chen, et al., *J Exp Med.*, 198 (12):1875-86 (2003). The expression of the three Akt isoforms at the protein level was analyzed by immunoblotting and quantified by densitometry analysis in the total protein lysates from iTregs and Th cells (same stimulation in absence of TGFβ). Although, Akt1 and Akt2 protein expression levels are similar in both cell types, similar to nTregs, the Akt3 protein expression was four to five fold higher in iTreg compare to Th condition (FIG. 12A).

Figure 12B:
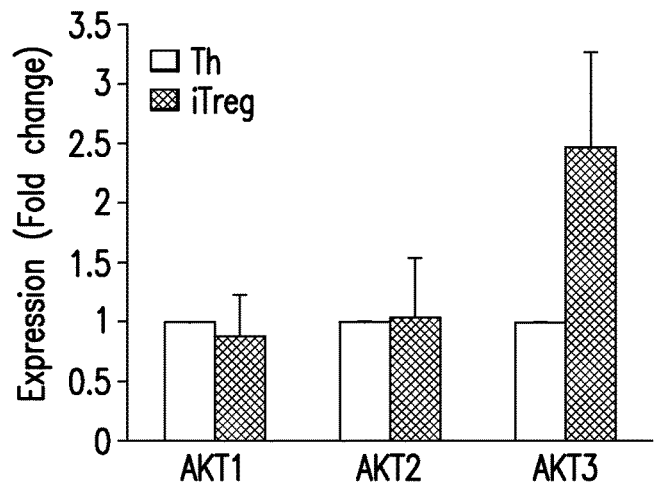
FIG. 12B is a bar graph showing the fold change in Akt1, Akt2, and Akt3 mRNA expression as determined by real time PCR analysis of RNA from CD4+ CD25− naïve T cells enriched from total splenocytes and stimulated in vitro with plate bound anti-CD3, soluble anti-CD28, and IL-2 in the presence (iTreg condition) or absence (Th condition) of TGFβ for 72 h (Fold change was calculated by the ΔΔCT method after normalizing to BACTIN and expression of different Akt isoforms are normalized to 1 in Th culture condition and compared the expression in iTreg culture condition; n=3, *P<0.05.).

Parallel assessment of mRNA levels showed that among all Akt isoforms Akt3 mRNA expression was also significantly higher in iTregs than Th cells, although not as dramatically as in nTregs (FIG. 12B).

To investigate activation of different Akt isoforms in iTreg the total protein lysates from Th and iTreg cells were immunoprecipitated with either Akt1 or Akt2 or Akt3 antibody followed by immunoblotting with phosphoserine antibody. Similar to nTregs, a preferential increase in phosphorylation of Akt3 (1.9 fold), while pAkt1 was less increased (1.4 fold) and pAkt2 level was decreased was observed in iTregs.

Example 8: Akt3 Isoform Regulates FoxP3 Induction During iTreg Conversion

Results

Figure 13A:
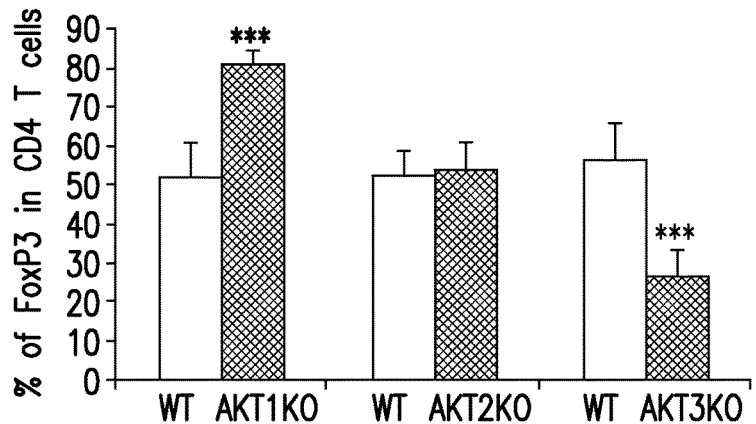
FIG. 13A is a bar graph showing the conversion of iTreg from naïve T cells as determined by flow cytometry and presented as percentage of Foxp3+ T cells in total CD4+ T cells (n=7, p<0.05) following enrichment of CD4+CD25− naïve T cells from total splenocytes and stimulation in vitro with plate bound anti-CD3, soluble anti-CD28, IL-2 and TGFβ for 72 h.

Next, the importance of Akt3 for conversion of CD25-Foxp3− into Foxp3 expressing cells was investigated. In order to do so, CD25-Foxp3− cells either from Akt KO or WT mice were cultured in the presence of TGFβ, TCR activation and IL-2 and Foxp3 expression was analyzed by flow cytometry. The results show that iTreg induction was significantly increased in absence of Akt1, unchanged in absence of Akt2 and significantly decreased in absence of Akt3 (FIG. 13A). These data indicate that the Akt3 isoform regulates FoxP3 induction and is required for iTreg conversion.

Figure 13B:
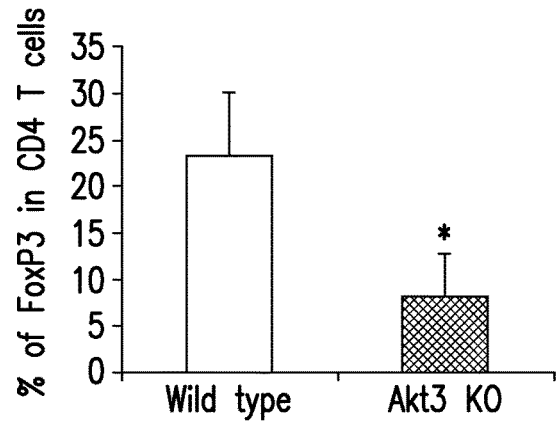
FIG. 13B is a bar graph showing in vivo iTreg conversion as the percentage of Foxp3+ T cells in total CD4+ T cells 72 hours after adoptive transfer of CFSE labeled naïve T cells from wild type and Akt3 knockout mice into TC1 tumor bearing (tumor size 500 mm$^2$) wild type mice (n=4, p<0.05).

To test whether Akt3 is important for iTreg induction also in in vivo, CFSE labeled CD4+CD25− Tconv cells from either Akt3 KO or WT mice were transferred into tumor-bearing animals and three days later analyzed the tumor-infiltrating CFSE+CD4+FoxP3+ T cell levels. The results indicate that in vivo conversion of Tconv cells into iTregs was significantly lower when cells were transferred from Akt3 KO mice compared to WT (FIG. 13B).

Next, TGFβ-mediated conversion of Tconv into iTregs was examined after lentiviral mediated knockdown of Akt3. Similar to Akt3 KO mice, Akt3 knockdown showed inhibition of induction of Foxp3 expressing cells.

Figure 14C:
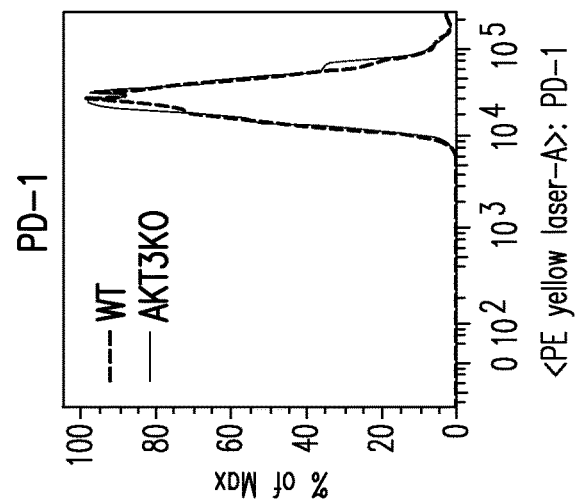
FIGS. 14A-14C are single parameter histograms showing expression of cell surface markers GITR (14A), CTLA4 (14B), and PD1 (14C) on CD4+CD25− naïve T cells were enriched from total splenocytes from wildtype and Akt3 knockout mice and stimulated in vitro with plate bound anti-CD3, soluble anti-CD28, and IL-2 in the presence of TGFβ (iTreg condition) for 72 h and analyzed by flow cytometry. iTreg phenotype was assess in iTreg (gated on CD4+Foxp3+) cells from Akt3 KO compare to that of wild type.
Figure 14B:
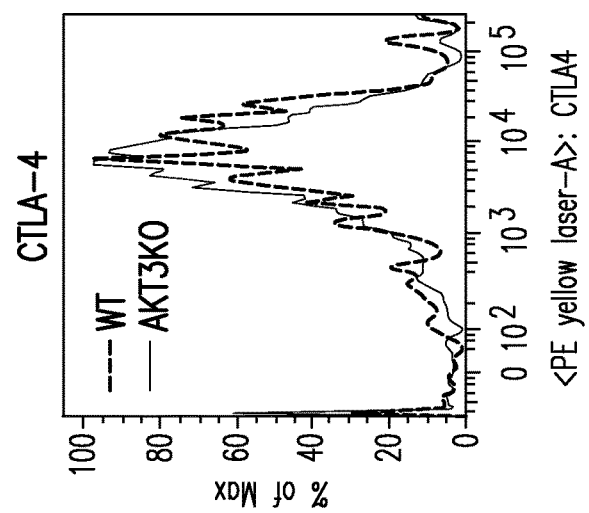
Figure 14A:
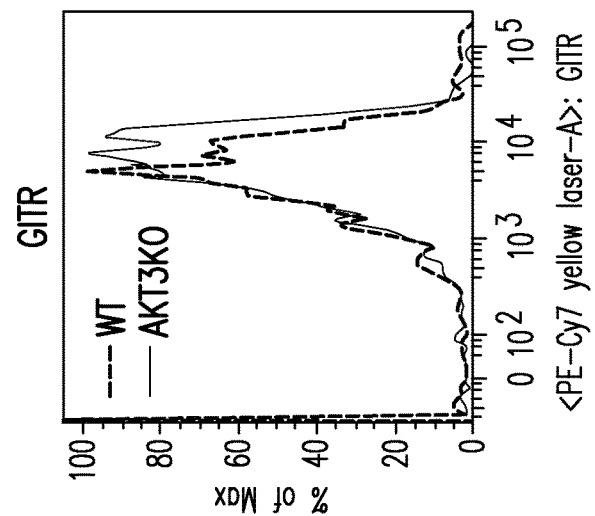

Example 9: Loss of Akt3 does not Alter Surface Marker Expression or Proliferation of iTregs Results After showing that Akt3 is involved in regulation of iTreg differentiation, the phenotypes of iTregs from Akt3 KO mice were compared to that in WT animals. Similar to nTregs, iTregs from Akt3 KO and WT mice expressed similar levels of Treg-specific surface markers (FIG. 14A-14B).

The effects of Akt3 knockout on the proliferation of iTregs cells in response to stimulation were also examined by utilizing a CFSE dilution assay. No differences in proliferation of iTregs from Akt3 KO mice compared to WT were detected (FIG. 15A-15B).

Example 10: Loss of Akt3 does not Impair the Suppressive Function of iTregs

Results

Figure 16:
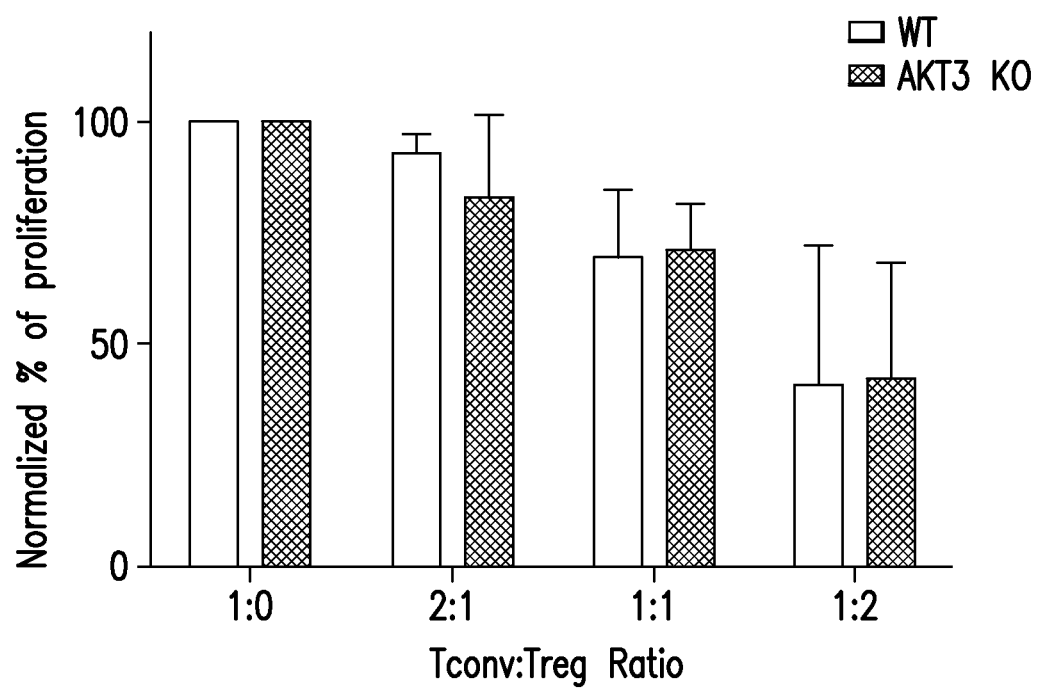
FIG. 16 is a bar graph showing in vitro suppressive activity of iTreg cells, assessed as the proliferation of naive CD4+ T cells (effector T cells isolated from total splenocytes (Teff)) activated by antibody to anti-CD3, anti CD28 and IL2 in the presence of various ratios (above plots) of normalized iTreg cells (1:0 non-stimulated) from wild-type or Akt3 knockout mice, measured as dilution of the cytosolic dye CFSE and analyzed by flow cytometry.
Figure 17A:
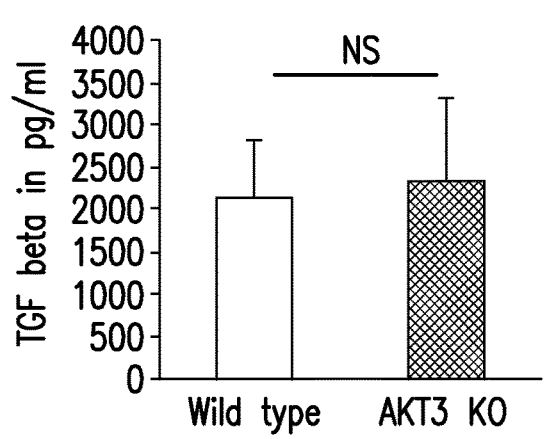
FIGS. 17A and 17B are bar graphs showing TGFβ in pg/ml (17A) and IL-10 in pg/ml (17B) cytokine content in supernatants of three days cultured CD4+CD25− cells enriched from total splenocytes, stimulated with anti-CD3, anti-CD28, IL-2 and TGFβ. The amounts of TGF-β and IL-10 were measured by ELISA. The end point read at absorbance at 450 nm, with the correction wavelength set at 570 nm. Values in wild type and Akt3 knockout are normalized according to flow cytometry based analysis of percentage of iTreg conversion (P<0.05, n=3).
Figure 17B:
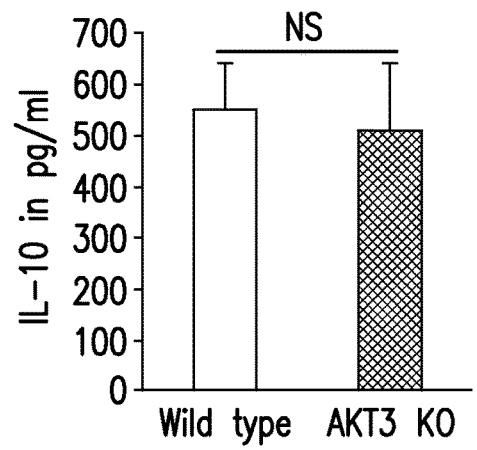

Next, the influence of Atk3 on the suppressive activity of iTregs was investigated. In co-culture experiments using CFSE-labeled WT Tconv cells and iTregs cells from either WT or Akt3 KO mice, iTregs from Akt3 KO mice were as functional as those from WT littermates, indicating that in contrast to nTregs the absence of Akt3 did not alter the function of iTregs in vitro (FIG. 16). In addition, the levels of TGFβ and IL10 expressed by iTregs in absence of Akt3 were also unchanged (FIG. 17A-17B).

Example 11: Akt3 is Important for iTreg Polarization

Results

To understand how Akt3 regulates iTreg polarization, signaling pathway interactions downstream of TGFβ-receptor and TCR/CD28 were investigated. It was previously proposed that PI3K-Akt pathway interacts with TGFβ-receptor signaling and Akt directly affects Smad proteins preventing their entrance into the nucleus and thus affecting the FoxP3 expression (Conery, et al., Nat Cell Biol., 6(4): 366-72 (2004)). To examine the role of Akt isoforms in this process, the nuclear translocation of Smad2 and Smad3 proteins in iTregs from Akt KO and WT mice were examined. Strikingly, it was discovered that both Smad2 and Smad3 were significantly decreased in the nucleus and cytosolic Smad2 was dramatically increased in iTregs from Akt3 KO mice. In contrast, nuclear translocation of both Smad molecules was increased and cytosolic Smad2 was decreased in absence of Akt1. The absence of Akt2 did not affect the levels of nuclear and cytosolic Smads.

Figure 18:
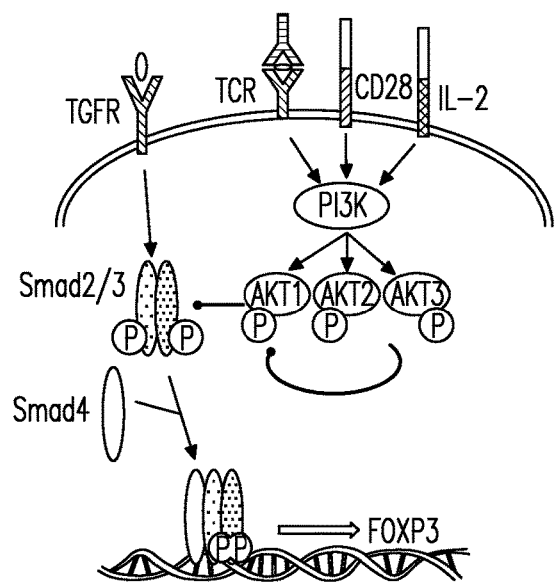
FIG. 18 is a diagram showing a proposed mechanism of regulation of iTreg by different Akt isoforms.

Taken together these data indicate that the possible isoform that interacts with Smads and responsible for their "neutralization" and thus FoxP3 decrease is Akt1. Thus, when Akt1 is absent there is no inhibition for Smads nuclear translocation and there is more protein detected in nucleus and more FoxP3 iTregs induced. The Akt3 isoform could block the Akt1-mediated inhibition of Smad nuclear translocation, since in the absence of Akt3 both total Akt1 and its phosphorylation are increased. Therefore, in Akt3 KO iTregs Smad nuclear translocation is decreased and less iTregs are induced (FIG. 18).

Figure 8A:
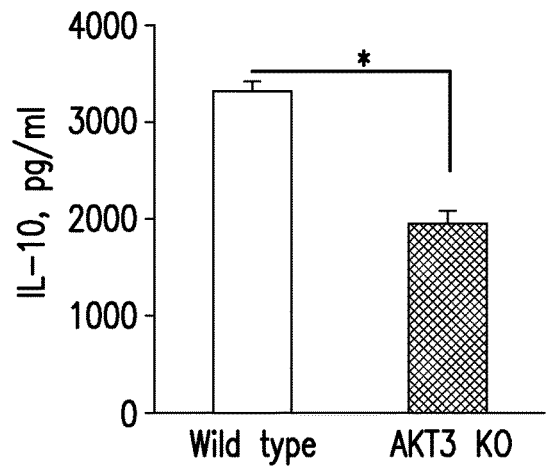
FIGS. 8A-8C are bar graphs showing the level of TGFβ (measured by ELISA) in supernatants Tconv (CD25−) and Treg (CD25+) CD4+ cells from WT (8A-8C), Akt1 (8B), Akt2 (8C), or Akt3 (8A) knockout mice enriched from total splenocytes and stimulated with anti-CD3, anti-CD28, and IL-2 for 72 h. The end point read at absorbance at 450 nm, with the correction wavelength set at 570 nm. (P<0.05, n=3).
Figure 8B:
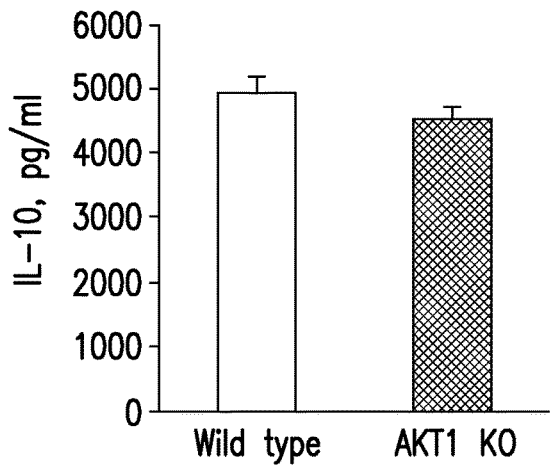
Figure 8C:
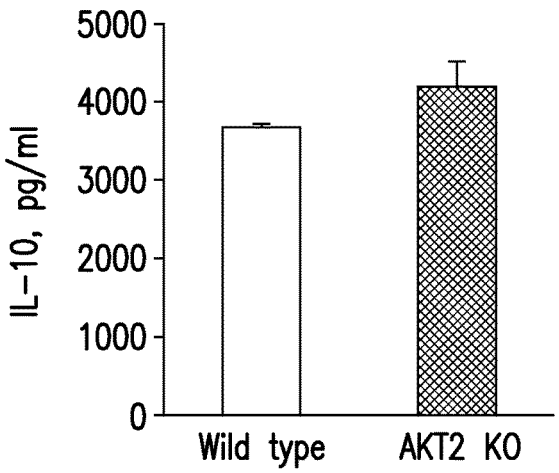

Collectively, the Examples above show that the Akt3 isoform is responsible for suppressive function of nTregs but not iTregs through inhibition of TGFβ and IL-10 expression (e.g., FIG. 8A-8C), and indicate that Akt3 is playing an important role in nTreg suppressive function and iTreg polarization. This functional diversity between nTregs and iTregs might be due to the differences in initial fate of Tregs that is predetermined for nTregs to depend on Akt3 isoform during the development in thymus, while the functions of iTregs are dictated by the environment and due to plasticity could not be depend on one isoform. In addition, the date indicate that in contrast to function, the conversion into iTregs is controlled by Akt3 via its inhibitory effect on Akt1 which "neutralizes" Smads nuclear translocation and inhibits FoxP3 expression.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of decreasing an immune suppressive response in a subject in need thereof comprising administering to the subject a composition comprising a compound that reduces the bioavailability of RAC-gamma serine/threonine-protein kinase (Akt3) by an amount effective to inhibit or reduce the secretion of Transforming Growth Factor beta (TGFβ) and interleukin-10 (IL-10) from natural regulatory T cells (nTregs) and to inhibit or reduce induction of induced regulatory T cells (iTregs) without impairing the suppressive function of iTregs, thereby decreasing the immune suppressive response.

2. The method of claim 1 wherein the subject has cancer or an infection.

3. The method of claim 2 wherein the cancer is selected from the group consisting of bladder, brain, breast, cervical, colo-rectal, esophageal, kidney, liver, lung, nasopharangeal, pancreatic, prostate, skin, stomach, uterine, ovarian, testicular and hematologic cancers.

4. A method of treating an infectious disease comprising administering to a subject with an infectious disease a composition comprising a compound that reduces the bioavailability of Rac-gamma serine/threonine-protein kinase (Akt3) in an amount effective to inhibit or reduce the secretion of Transforming Growth Factor beta (TGFβ) and interleukin-10 (IL-10) from natural regulatory T cells (nTregs) and to inhibit or reduce induction of induced regulatory T cells (iTregs) without impairing the suppressive function of iTregs, thereby treating the infectious disease.

5. The method of claim 2 wherein the infectious disease is caused by bacterium, virus, protozoan, helminth, or other microbial pathogen.

6. The method of claim 1, wherein the compound that reduces the bioavailability of Akt3 is selected from the group consisting of inhibitory Akt3 polypeptides that bind to one or more substrates of Akt3; small molecules that bind to and inhibit occupancy or activity of the Akt3 kinase domain; substrate mimics that bind to Akt3 and serves as a molecular sink for Akt3 kinase activity; and inhibitory nucleic acids that reduce expression of Akt3.

* * * * *